(12) United States Patent
Kleinsek et al.

(10) Patent No.: US 7,799,325 B2
(45) Date of Patent: Sep. 21, 2010

(54) REMOVAL OF HYPERTROPHIC SCARS

(76) Inventors: Donald A. Kleinsek, W5036N CTHA, Elkart Lake, WI (US) 53020; Adriana Soto, W5036N CTHA, Elkart Lake, WI (US) 53020

( * ) Notice: Subject to any disclaimer, the term of this patent is extended or adjusted under 35 U.S.C. 154(b) by 219 days.

(21) Appl. No.: 11/982,321

(22) Filed: Nov. 1, 2007

(65) Prior Publication Data

US 2008/0138324 A1 Jun. 12, 2008
US 2009/0016996 A2 Jan. 15, 2009

Related U.S. Application Data

(63) Continuation-in-part of application No. 10/129,180, filed as application No. PCT/US00/30623 on Nov. 6, 2000.

(60) Provisional application No. 60/163,734, filed on Nov. 5, 1999.

(51) Int. Cl.
*A61K 35/12* (2006.01)
*A61P 17/02* (2006.01)

(52) U.S. Cl. .................... 424/93.7; 435/325

(58) Field of Classification Search ............... None
See application file for complete search history.

(56) References Cited

U.S. PATENT DOCUMENTS

| | | |
|---|---|---|
| 3,600,718 A | 8/1971 | Boone |
| 3,665,520 A | 5/1972 | Perras et al. |
| 3,911,503 A | 10/1975 | Hankin |
| 3,949,073 A | 4/1976 | Daniels et al. |
| 4,100,627 A | 7/1978 | Brill, III |
| 4,139,619 A | 2/1979 | Chidsey, III |
| 4,172,298 A | 10/1979 | Rechenberg |
| 4,234,599 A | 11/1980 | Van Scott et al. |
| 4,298,998 A | 11/1981 | Naficy |
| 4,377,584 A | 3/1983 | Rasmusson et al. |
| 4,401,308 A | 8/1983 | Sakaguchi et al. |
| 4,424,208 A | 1/1984 | Wallace et al. |
| 4,488,911 A | 12/1984 | Luck et al. |
| 4,551,270 A | 11/1985 | Danos et al. |
| 4,582,640 A | 4/1986 | Smestad et al. |
| 4,612,331 A | 9/1986 | Barratt et al. |
| 4,642,117 A | 2/1987 | Nguyen et al. |
| 4,684,522 A | 8/1987 | Marissal et al. |
| 4,760,071 A | 7/1988 | Rasmusson et al. |
| 4,772,284 A | 9/1988 | Jefferies et al. |
| 4,790,848 A | 12/1988 | Cronin |
| 4,803,075 A | 2/1989 | Wallace et al. |
| 4,837,379 A | 6/1989 | Weinberg |
| 4,840,628 A | 6/1989 | Cavon |
| 4,882,166 A | 11/1989 | Graham et al. |
| 4,919,664 A | 4/1990 | Oliver et al. |
| 4,969,912 A | 11/1990 | Kelman et al. |
| 5,002,071 A | 3/1991 | Harrell |
| 5,030,451 A | 7/1991 | Trebosc et al. |
| 5,032,508 A * | 7/1991 | Naughton et al. ............. 435/32 |
| 5,037,803 A | 8/1991 | Gueyne et al. |
| 5,116,605 A | 5/1992 | Alt |
| 5,140,200 A | 8/1992 | Stanton |
| 5,192,312 A | 3/1993 | Orton |
| 5,194,259 A | 3/1993 | Soudant et al. |
| 5,197,983 A | 3/1993 | Berman et al. |
| 5,199,942 A | 4/1993 | Gillis |
| 5,215,759 A | 6/1993 | Mausner |
| 5,332,802 A | 7/1994 | Kelman et al. |
| 5,366,498 A | 11/1994 | Brannan et al. |
| 5,376,117 A | 12/1994 | Pinchulk et al. |
| 5,422,261 A | 6/1995 | Lee et al. |
| 5,449,757 A | 9/1995 | Serrero |
| 5,480,644 A | 1/1996 | Freed |
| 5,510,102 A | 4/1996 | Cochrum |

(Continued)

FOREIGN PATENT DOCUMENTS

| | | |
|---|---|---|
| EP | 0106501 B1 | 4/1984 |
| FR | 2554344 | 5/1985 |

OTHER PUBLICATIONS

Garbin et al., "Covering by a flap induces apoptosis of granulation tissue myofibroblasts and vascular cells", Wound Repair and Regeneration, 1996, vol. 4, pp. 244-251.*

(Continued)

*Primary Examiner*—Jon P Weber
*Assistant Examiner*—Laura Schuberg

(57) ABSTRACT

An embodiment of the invention includes methods for the long-term augmentation and/or repair of skin defects (scars, skin laxness, skin thinning, and skin augmentation), cellulite, breast tissue, wounds and burns, urological and gastroesophageal sphincter structures, hernias, periodontal disease and disorders, tendon and ligament tears and baldness, by the injection or direct surgical placement/implantation of autologous cultured cells and/or cultured cell-produced extracellular matrix that is derived from connective tissue, dermis, fascia, lamina propria, stroma, adipose tissue, muscle, tendon, ligament or the hair follicle. The corrective application is done on tissue proximal or within the area of the defect. The method involves retrieving viable cells from the subject, a neonate or human fetus. Alternatively, the corrective application involves the cells placed in a matrix, preferably comprised of autologous extracellular matrix constituents as a three-dimensional structure or as a suspension, prior to placement into a position with respect to the subject's defect. In a further embodiment, the preferable autologous extracellular matrix constituents are collected from culture and placed in a position with respect to the subject's defect.

4 Claims, No Drawings

U.S. PATENT DOCUMENTS

| | | |
|---|---|---|
| 5,516,532 A | 5/1996 | Atala et al. |
| 5,516,779 A | 5/1996 | Von Langen et al. |
| 5,523,090 A | 6/1996 | Znaiden et al. |
| H1610 H | 11/1996 | Lou et al. |
| 5,587,396 A | 12/1996 | Smith |
| 5,591,444 A | 1/1997 | Boss, Jr. |
| 5,599,788 A | 2/1997 | Purchio et al. |
| 5,656,478 A | 8/1997 | Tanagho et al. |
| 5,667,778 A | 9/1997 | Atala |
| 5,709,854 A | 1/1998 | Griffith-Cima et al. |
| 5,759,190 A | 6/1998 | Vibe-Hansen et al. |
| 5,763,399 A | 6/1998 | Lee |
| 5,830,708 A | 11/1998 | Naughton |
| 5,842,477 A | 12/1998 | Naughton et al. |
| 5,858,390 A | 1/1999 | Boss, Jr. |
| 5,863,531 A | 1/1999 | Naughton et al. |
| 5,888,551 A | 3/1999 | Jimenez et al. |
| 6,044,846 A | 4/2000 | Edwards |
| 6,060,053 A | 5/2000 | Atala |
| 6,092,528 A | 7/2000 | Edwards |
| 6,156,032 A | 12/2000 | Lennox |
| 6,325,798 B1 | 12/2001 | Edwards et al. |
| 6,355,239 B1 | 3/2002 | Bruder et al. |
| 6,432,710 B1 | 8/2002 | Boss, Jr. et al. |
| 6,497,875 B1 | 12/2002 | Sorrell et al. |
| 6,802,841 B2 | 10/2004 | Utley et al. |
| 6,830,762 B2 | 12/2004 | Baugh et al. |
| 6,866,842 B1 | 3/2005 | Chancellor et al. |
| 6,878,383 B2 | 4/2005 | Boss, Jr. et al. |
| 7,115,274 B2 | 10/2006 | Keller et al. |
| 2002/0055786 A1 | 5/2002 | Atala |
| 2007/0065415 A1 | 3/2007 | Kleinsek et al. |

OTHER PUBLICATIONS

Keller et al., "Safety of Injectable Autologous Human Fibroblasts", Bulletin of Experimental Biology and Medicine, Aug. 2000, vol. 130, No. 8, pp. 786-789.*

* cited by examiner

REMOVAL OF HYPERTROPHIC SCARS

REFERENCE TO RELATED APPLICATIONS

This application is a continuation-in-part of U.S. patent application Ser. No. 10/129,180, filed on May 3, 2002, which claims priority to PCT/US00/30623, filed Nov. 6, 2000, which claims priority to 60/163,734, filed Nov. 5, 1999, which patent applications are hereby incorporated by reference herein.

FIELD OF INVENTION

The present invention relates to repair or long-term augmentation of defects in human tissues that primarily increase in incidence with age.

INTRODUCTION TO THE INVENTION

Reference should be had to International Patent Application Publication No. WO 98/40027, as well as the following background, for mammalian cells derived from in vitro cell culture and extracellular matrix from such cells in culture, that may be used in accordance with the present invention to repair or augment human tissue defects.

A. In vitro Cell Culture

The majority of in vitro vertebrate cell cultures are grown as monolayers on an artificial substrate which is continuously bathed in a nutrient medium. The nature of the substrate on which the monolayers may be grown may be either a solid (e.g., plastic) or a semi-solid (e.g., collagen agar). Currently, disposable plastics have become a preferred substrate for cell culture.

While the growth of cells in two-dimensions is frequently used for the preparation and examination of cultured cells in vitro, it may lack the characteristics of intact, tissue in vivo tissue which, for example, includes cell-cell and cell-matrix interactions. Therefore, in order to characterize these functional and morphological interactions, various investigators have examined the use of three-dimensional substrates in such forms as a collagen gel (Yang et al., Cancer Res. 41:1027 (1981); Douglas et al., In Vitro 16:306 (1980); Yang et al., Proc. Nat'l Acad. Sci. 2088 (1980)) cellulose sponge (Leighton et al., J. Nat'l Cancer Inst. 12:545 (1951)), collagen-coated cellulose sponge (Leighton et al., Cancer Res. 28:286 (1968)), and GELFOAM® (Sorour et al., J. Neurosurq. 43:742 (1975)).

Typically, these aforementioned three-dimensional substrates are inoculated with the cells to be cultured, which subsequently penetrate the substrate and establish a "tissue-like" histology similar to that found in vivo. Several attempts to regenerate "tissue-like" histology from dispersed monolayers of cells utilizing three-dimensional substrates have been reported. For example, three-dimensional collagen substrates have been utilized to culture a variety of cells including breast epithelium (Yang, Cancer Res. 41:1021 (198.1)), vascular epithelium (Folkman et al., Nature 288:551 (1980)), and hepatocytes (Sirica et al., Cancer Res. 76:3259 (1980)). However, long-term culture and proliferation of cells in such systems has not yet been achieved. Prior to the present invention, a two or three-dimensional substrate had not been utilized in the total autologous in vitro culture of cells or tissues derived from many connective tissue sources, such as dermis, fascia, lamina propria of gingiva and ureteral tissue, adipose tissue and cartilage.

B. Augmentation and/or Repair of Dermal, Subcutaneous (Hypodermis) and Fascial Tissues In the practice of cosmetic and reconstructive plastic surgery, it is frequently necessary to employ the use of various injectable materials to augment and/or repair defects of the subcutaneous or dermal tissue, thus effecting an aesthetic result. Non-biological injectable materials (e.g., paraffin) were first utilized to correct facial contour defects as early as the late nineteenth century. However, numerous complications and the generally unsatisfactory nature of long-term aesthetic results caused the procedure to be rapidly abandoned. More recently, the use of injectable silicone became prevalent in the 1960's for the correction of minor defects, although various inherent complications also limited the use of this substance. Complications associated with the utilization of injectable liquid silicone include local and systemic inflammatory reactions, formation of scar tissue around the silicone droplets, rampant and frequently distant, unpredictable migration throughout the body, and localized tissue breakdown. Due to these potential complications, silicone is not currently approved for general clinical use. Although the original proponents of silicone injection have continued experimental programs utilizing specially manufactured "Medical Grade" silicone (e.g., Dow Corning's MDX 4.4011®) with a limited number of subjects, it appears highly unlikely that its use will be generally adopted by the surgical community. See e.g., Spira and Rosen, Clin. Plastic Surgery 20:181 (1993); Matton et al., Aesthetic Plastic Surgery 9:133 (1985).

It has also been suggested to compound extremely small particulate species in a lubricious material and inject such micro-particulate media subcutaneously for both soft and hat tissue augmentation and repair. However, success has been heretofore limited. For example, bioreactive materials such as hydroxyapatite or cordial granules (osteo conductive) have been utilized for the repair of hard tissue defects. Subsequent undesirable micro-particulate media migration and serious granulomatous reactions frequently occur with the injection of this material. These undesirable effects are well-documented with the use of such materials as polytetrafluoroethylene (TEFLON®) spheres of small-diameter (~90% of particles having diameters of $\leq$30 µm) in glycerin. See e.g., Malizia et al., JAMA 251:3277 (1984). Additionally, the use of very small-diameter particulate spheres (~1-20 µm) or small elongated fibrils (~1-30 µm in diameter) of various materials in a biocompatible fluid lubricant as injectable implant composition are disclosed in U.S. Pat. No. 4,803,075. However, while these aforementioned materials create immediate augmentation and/or repair of defects, they also have a tendency to migrate and be reabsorbed from the original injection site.

The poor results initially obtained with the use of non-biological injectable materials prompted the use of various non-immunogenic, proteinaceous materials (e.g., bovine collagen and fibrin matrices). Prior to human injection, however, the carboxyl- and amino-terminal peptides of bovine collagen must first be enzymatically degraded, due to its highly immunogenic nature. Enzymatic degradation of bovine collagen yields a material, atelocollagen, which can be used in limited quantities in patients pre-screened to exclude those who are immunoreactive to this substance. The methodologies involved in the preparation and clinical utilization of atelocollagen are disclosed in U.S. Pat. Nos. 3,949,073; 4,424, 208; and 4,488,911. Atelocollagen has been marketed as ZYDERM® brand atelocollagen solution in concentrations of 35 mg/ml and 65 mg/ml. Although atelocollagen has been widely employed, the use of ZYDERM solution has been associated with the development of antibovine antibodies in approximately 90% of patients and with overt immunological complications in 1-3% of patients. See DeLustro et al., Plastic and Reconstructive Surgery 79:581 (1987).

Injectable atelocollagen solution also was shown to be absorbed from the injection site, without replacement by host material, within a period of weeks to months. Clinical protocols calling for repeated injections of atelocollagen are, in practice, primarily limited by the development of immunogenic reactions to the bovine collagen. In order to mitigate these limitations, bovine atelocollagen was further processed by cross-linking with 0.25% glutaraldehyde, followed by filtration and mechanical shearing through fine mesh. The methodologies involved in the preparation and clinical utilization of this material are disclosed in U.S. Pat. Nos. 4,582,640 and 4,642,117. The modified atelocollagen was marketed as ZYPLAST® brand cross-linked bovine atelocollagen. The projected advantages of cross-liking were to provide increased resistance to host degradation, however this was offset by an increase in solution viscosity. In addition, cross-linking of the bovine atelocollagen was found to decrease the number of host cells which infiltrated the injected collagen site. The increased viscosity, and in particular irregular increased viscosity resulting in "lumpiness," not only rendered the material more difficult to utilize, but also made it unsuitable for use in certain circumstances. See e.g., U.S. Pat. No. 5,366,498. In addition, several investigators have reported that there is no or marginally increased resistance to host degradation of ZYPLAST cross-linked bovine atelocollagen in comparison to that of the non-cross-linked ZYDERM atelocollagen solution and that the overall longevity of the injected material is, at best, only 4-6 months. See e.g., Ozgentas et al., Ann. Plastic Surgery 33:171 (1994); and Matti and Nicolle, Aesthetic Plastic Surgery 14:227 (1990).

Moreover, bovine atelocollagen cross-linked with glutaraldehyde may retain this agent as a high molecular weight polymer which is continuously hydrolyzed, thus facilitating the release of monomeric glutaraldehyde. The monomeric form of glutaraldehyde is detectable in body tissues for up to 6 weeks after the initial injection of the cross-linked atelocollagen. The cytotoxic effect of glutaraldehyde on in vitro fibroblast cultures is indicative of this substance's not being an ideal cross-linking agent for a dermal equivalent which is eventually infiltrated by host cells and in which the bovine atelocollagen matrix is rapidly degraded, thus resulting in the release of monomeric glutaraldehyde into the bodily tissues and fluids. Similarly, chondroitin-6-sulfate (GAG), which weakly binds to collagen at neutral pH, has also been utilized to chemically modify bovine protein for tissue graft implantation. See Hansborough and Boyce, JAMA 136:2125 (1989). However, like glutaraldehyde, GAG may be released into the tissue causing unforeseen long-term effects on human subjects. GAG has been reported to increase scar tissue formation in wounds, which is to be avoided in grafts. Additionally, a reduction of collagen blood clotting capacity may also be deleterious in the application in bleeding wounds, as fibrin clot contributes to an adhesion of the graft to the surrounding tissue.

The limitations which are imposed by the immunogenicity of both modified and non-modified bovine atelocollagen have resulted in the isolation of human collagen from placenta (see e.g., U.S. Pat. No. 5,002,071); from surgical specimens (see e.g., U.S. Pat. Nos. 4,969,912 and 5,332,802); and cadaver (see e.g., U.S. Pat. No. 4,882,166). Moreover, processing of human-derived collagen by cross-linking and similar chemical modifications is also required, as human collagen is subject to analogous degradative processes as is bovine collagen Human collagen for injection, derived from a sample of the patient's own tissue, is currently available and is marketed as AUTOLOGEN®. It should be noted, however, that there is no quantitative evidence which demonstrates that human collagen injection results in lower levels of implant degradation than that which is found with bovine collagen preparations. Furthermore, the utilization of autologous collagen preparation and injection is limited to those individuals who have previously undergone surgery, due to the fact that the collagen is produced is derived from the tissue removed during the surgical procedure. Therefore, it is evident that, although human collagen circumvents the potential for immunogenicity exhibited by bovine collagen, it fails to provide long-term therapeutic benefits and is limited to those patients who have undergone prior surgical procedures.

An additional injectable material currently in use as an alternative to atelocollagen augmentation of the subjacent dermis consists of a mixture of gelatin powder, $\epsilon$-aminocaproic acid, and the patient's plasma marketed as FIBREL®. See Multicenter Clinical Trial, J. Am. Acad. Dermatology 16:1155 (1987). The action of the FIBREL product appears to be dependent upon the initial induction of a sclerogenic inflammatory response to the augmentation of the soft tissue via the subcutaneous injection of the material. See e.g., Gold, J. Dermatologic Surg. Oncology, 20:586 (1994). Clinical utilization of the FIBREL product has been reported to often result in an overall lack of implant uniformity. (i.e., "lumpiness") and longevity, as well as complaints of patient discomfort associated with its injection. See e.g., Millikan et al., J. Dermatologic. Surg. Oncology, 17:223 (1991). Therefore, in conclusion, none of the currently utilized protein-based injectable materials appears to be totally satisfactory for the augmentation and/or repair of the subjacent dermis and soft tissue.

The various complications associated with the utilization of the aforementioned materials have prompted experimentation with the implantation (grafting) of viable, living tissue to facilitate augmentation and/or repair of the subjacent dermis and soft tissue. For example, surgical correction of various defects has been accomplished by initial removal and subsequent re-implantation of the excised adipose tissue either by injection (Davies et al., Arch. of Otolaryngology-Head and Neck Surgery 121:95 (1995); McKinney & Pandya; Aesthetic Plastic Surgery 18:383 (1994); and Lewis, Aesthetic Plastic Surgery, 17:109 (1993)) or by the larger scale surgical-implantation (Ersck, Plastic & Reconstructive Surgery 87:219 (1991)). To perform both of the aforementioned techniques a volume of adipose tissue equal or greater than is required for the subsequent augmentation or repair procedure must be removed from the patient. Thus, for large scale repair procedures the amount of adipose tissue which can be surgically-excised from the patient may be limiting. In addition, other frequently encountered difficulties with the aforementioned methodologies include non-uniformity of the injectate, unpredictable longevity of the aesthetic effects, and a 4-6 week period of post-injection inflammation and swelling.

Living skin equivalents have been examined as a methodology for the repair and/or replacement of human skin. Split thickness autographs, epidermal autographs (cultured autogenic keratinocytes), and epidermal allographs (cultured allogenic keratinocytes) have been used with a varying degree of success. However, unfortunately, these forms of treatment have all exhibited numerous disadvantages. For example, split thickness autographs generally show limited tissue expansion, require repeated surgical operations, and give rise to unfavorable aesthetic results. Epidermal autographs require long periods of time to be cultured, have a low success ("take") rate of approximately 30-48%, frequently form spontaneous blisters, exhibit contraction to 60-70% of their original size, are vulnerable during the first 15 days of engraftment, and are of no use in situations where there is both epidermal and dermal tissue involvement. Similarly, epidermal allografts (cultured allogenic keratinocytes) exhibit many of the limitations which are inherent in the use of epidermal autographs, in addition to graft rejection. Additional methodologies have been examined which involve the utilization of irradiated cadaver dermis. However, this too has met with limited success due to, for example, graft rejection and unfavorable aesthetic results. Living skin equivalents comprising a dermal layer of rodent fibroblast cells cast in soluble collagen and an epidermal layer of cultured rodent keratinocytes have been successfully grafted as allografts onto Sprague Dawley rats by Bell et al., J. Investigative Dermatology 81:2 (1983). Histological examination of the engrafted tissue revealed that the epidermal layer had fully differentiated to form desmosomes, tonofilaments, keratohyalin, and a basement layer. However, subsequent attempts to reproduce the living skin equivalent using human fibroblasts and keratinocytes has met with only limited success. In general, the keratinocytes failed to fully differentiate to form a basement layer and the dermo-epidermal junction was a straight line.

Scarring is a skin defect, in response to various environmental and physiological insults, affecting the layers of the skin with variable depth. Scars can be depressions or can be hypertrophic, often the result of excess collagen production. Skin laxity or "sagginess" is a skin defect due to loss of skin tone with age. Additionally skin thinning is an age-dependent defect. Augmentation of skin thickness is useful for an improved cosmetic look as well as a substitute for certain surgeries, such as for penile enlargement. In a preferred embodiment of this invention the injection into those defects of compositions of fibroblasts harvested from the dermis or fascia, expanded in culture, and then injected into the deeper layers of the skin: from the fascia to the dermis (upper, mid, lower portion).

The present invention includes the following preferred methodologies and compositions for the repair and/or augmentation of skin defects comprised of scars, skin laxness or skin thinning or the need for skin thickening: Placement into various layers of the skin (fascial, subcutaneous, dermal) or directly into a "pocket" created in the region to be repaired or augmented by: (1) the injection of autologously cultured stromal or connective tissue fibroblasts and/or cultured fibroblast-produce extracellular matrix such as in the preferred embodiment dermal fibroblasts. Alternatively or in addition, fascial and/or lamina propria and/or stromal fibroblasts and/or adipocytes or pre-adipocytes are selected or (2) the surgical engraftment of "strands" derived from the aforementioned autologous fibroblasts or cells and/or cultured fibroblast-produced extracellular matrix which are cultured in such a manner as to form a three-dimensional "tissue-like" structure similar to that which is found in vivo.

Moreover, the present invention also differs on a two-dimensional level in that "true" autologous culture and preparation of the cells and/or extracellular matrix composition is performed by the preferred embodiment that utilizes the patient's own cells and serum for in vitro culture.

C. Augmentation and Repair of Cellulite

Cellulite is the lay term that describes the abnormal lumpy/ dimple skin appearance mainly in the thighs, hips and buttocks of women. Cellulite has a high incidence in the world's population, affecting approximately between 50 to 80% of women of every age group, from post-puberty until post-menopause. Cellulite is usually more severe in overweight to obese individuals, but it is commonly observed in those with a normal body mass index (BMI) or even in underweight women.

It has been reported that cellulite improves after menopause and it is not present in men with normal levels of androgen hormones. This fact calls for an etiologic theory relating the skin defect with the feminine hormonal environment, with particular regard to the estrogens and their role in determining the way fat is stored subcutaneously, such as in the gluteal/thigh areas. After menopause, along with increased levels of androgens, the fat is deposited in a pattern simulating masculinity, e.g. around the visceral organs and the abdomen.

Fat, in the form of triglyceride, is stored in the subcutaneous layer of skin within fat cells (adipocytes). A group of these adipocytes form a fat lobe. Several fat lobes will form a fat lobule that can measure up to 1 cm and is surrounded by blood capillaries. These lobules are located underneath the skin surface and on top of the muscular layer. Connective tissue bands of fibers running perpendicular to the skin connect the surface of the skin to the muscular layer forming pockets that harbor the fat lobes. Excess fat can fill these pockets to a point in which the connective band can not stretch more and hence, will pull the surface of the skin downward. This movement creates dimples, commonly referred to as "cottage cheese", "orange skin" appearance or the "mattress phenomenon". As shown histologically, some degree of inflammation and scarring occurs.

At the physiological level net fat storage or removal within the adipocyte is dependent on a balance between uptake of dietary triglycerides and breakdown of the storage triglycerides within the adipocyte, and removal of free fatty acids for energy utilization. Lipolysis (breakdown of the fat in the cell) occurs with the action of enzymes (lipases) controlled by hormones that interact with alpha-2 and beta adipocyte surface receptors, thus, serving as activators of energy metabolism. These physiological events are the basis of several pharmacological compounds used to treat cellulite. These compounds, applied in the form of creams or massage oils, theoretically claim to stimulate lipolysis and are listed in patents as described below.

It is claimed that different skin treatments with xanthines, such as caffeine, theophylline or aminophylline, act as phosphodiesterase inhibitors and stimulate lipolysis (European Patent No. 0 728 472 A2, French Patent Nos. 2,499,405; 2,554,344, and U.S. Pat. Nos. 4,684,522; 5,030,451; 5,037, 803; 5,215,759). The use of these components for the treatment of cellulite confers drug-use issues (e.g., long-term use at high concentrations) preventing the components for extended and over-the-counter use and hence, limiting marketing.

Other treatments describe the use of inositol phosphate, particularly phytic acid, in an acceptable carrier, (European Patent No. 0 728 471 A2). Xanthine, combined with an inositol phosphoric acid and/or hydroxy acid is described in U.S. Pat. No. 5,523,090. Other treatments use a product containing cellulose (International Patent No. WO 96/31192), a cream containing aromatase inhibitors acting as anti-oestrogen compounds (International Patent No. WO 97/36570) or a composition containing niacinamide, (International Patent No. WO 99/47112). Other compounds include an alpha-2 blocker compound as described in U.S. Pat. No. 5,194,259, betulinic acid, (European Patent No. 0 717 983 A1), and several type of alpha-hydroxy acids, (U.S. Pat. Nos. 4,234, 599; 4,612,331; 5,116,605). A new compound that increases the trans-epidermal water loss (TEWL) is a cream containing retinoic acid, lactic acid, cerebrosides and secondary compounds such as diuretics, anti-oxidants and anti-irritants (U.S. Pat. No. 5,587,396 and International Patent No. 97/14412). Lately a new and controversial supplement product (Cellasene™, Rexall Sundown Corp) was launched in the U.S after some years of use in Europe. This is a mixture of several herbs including ginko biloba, grape-seed extract, sweet clover extract, borage seed oil, fish oil and bladderwrack, among other ingredients.

Another popular way to treat cellulite is to use physical forces to improve venous and lymphatic drainage of the area by massage, manual or by means of several devices, such as scroll chuck components (U.S. Pat. No. 4,401,308), or vacuum like devices (Endermologie™ from LPG USA, Silhouette™ or SilkLight™ from ESC Medical Systems).

Commonly, more aggressive approaches to cellulite combine several types of the therapies described above, along with exercise and low-fat diets, but in general, only very little and temporary progress has been reported for treating this prevalent condition.

The present invention includes the following preferred methodologies and compositions for the repair and/or augmentation of cellulite: (1) the injection of autologously cultured fibroblasts and cultured fibroblast-produced extracellular matrix into various layers of the skin. The cells can be dermal and/or fascial fibroblasts and/or stromal fibroblasts that are placed by injection into various layers of the dermis and/or hypodermis (subcutaneous) or by injection directly into a "pocket" (e.g. cutting of the connective tissue strands between dermis and fascia) created in the region to be repaired or augmented, or (2) the surgical engraftment of "strands" derived from the aforementioned autologous cultured fibroblasts and fibroblast-produced extracellular matrix and which are cultured in such a manner as to form a three-dimensional "tissue like" structure similar to that which is found in vivo.

D. Augmentation and Repair of Wounds

Mammalian wound healing is primitive in comparison with that of the "lower" forms of life. In the latter, the healing process calls for regeneration, whereas in the former, reparation involves the mechanisms of inflammation, extracellular matrix deposition, epithelialization and contraction, leading to scarring. The ultimate goal in wound healing is to turn the process into a regenerative one as well.

Wounds belong to two general categories: acute and chronic. Acute wounds heal by following an orderly and timely process in which substantial reparation of the anatomy of the tissue and its functional integrity is regained. Chronic wounds fail to repair and therefore the anatomy and functionality of the tissue is not achieved (Cohen et al., in Schwartz S. I., Principles of Surgery, $7^{th}$ Ed., pp 263, McGraw Hill, New York, 1999; Adzick N. in Sabinston D.C., Sabinston's Textbook of Surgery, $15^{th}$ Ed., pp 207, W B Saunders, Philadelphia, 1997). There are four types of wound closure. 1) The primary type occurs when the borders of the acutely disrupted tissue is approximated by sutures, staples, tape, etc; 2) The delayed primary type occurs when the margins of the wound are deliberately left separated for several days, because of extensive tissue trauma containing significant tissue bacterial contamination or foreign bodies. The therapeutic approach is to keep the wound moist and dressed in the presence of antibiotics for a natural healing process; 3) Spontaneous or secondary wound closure occurs when the margins of the wound move together by means of the physiological process of contraction; 4) Partial-thickness wounds heal by the process of epithelialization via epithelial cell division and migration.

There are four phases of normal wound healing. 1) Coagulation is the first phase. Damaged blood vessels hemorrhage and vasoconstrict, the endothelial cells release several vasoactive compounds attracting several type of cells, including platelets which form a clot and fibroblasts, which produce cytokines modulating most of the subsequent healing events. 2) Inflammation is the second phase. Leukocytes migrate to the wound. In particular, macrophages and polymorphonuclear types produce cytokines or "growth factors" to regulate connective tissue matrix deposition by the fibroblasts. 3) Fibroplasia is the third phase. This is the structural phase in which collagen and other extracellular proteins are synthesized and deposited by fibroblasts that result in wound strength and integrity. 4) Remodeling is the last phase. Inflammation diminishes, angiogenesis ceases and the fibroplasia ends. An equilibrium is established between collagen synthesis and degradation by the action of enzymes, such as collagenase, that destroy the excess collagen. The fibrous repair is imperfect, but functional (Cohen I K et al., in Wound Healing: Biochemical and Clinical Aspects, Philadelphia, W B Saunders, 1992).

One of the latest breakthroughs in understanding wound healing is the knowledge of the importance of several cell released substances call cytokines, that provide the signals to start the several phases involving healing (Schaffer M. et al., Br J Surg. 85:444, 1998). They are the "wound hormones" and regulate the proliferation of cells, attract cells to the wound site and direct cells to produce the required macromolecules for extracellular matrix repair. The nomenclature of at least twelve cytokines involved in wound healing is complex, in which several cytokines are named after the cells that produce them and others by their function. Platelets produce several cytokines, including PDGF (Platelet Derived Growth Factor), that attracts several cell types into the wound such as leukocytes, fibroblasts, and smooth muscle cells. PDGF also stimulates fibroblasts to produce such extracellular macromolecules as fibronectin, hyaluronic acid and collagen and may stimulate wound contraction. Epithelial growth factor (EGF) stimulates epithelial cell migration and mitosis. TGF-beta, is produced by almost every cell type involved in wound healing and one of its most important roles is the induction of collagen synthesis and deposition by fibroblasts (Sporn et al., J Cell Biol 105:1039, 1987, Border et al., N. Engl. J. Med., 331: 1286, 1994). Fibroblast growth factor (FGF) is a group of cytokines involved in angiogenesis and fibroblast migration and division. There are many other cytokines besides the ones described above. The roles and mechanisms that regulate their production during wound healing is not well understood. (Cohen et al., in Schwartz S. I., Principles of Surgery, $7^{th}$ Ed., pp 263, McGraw Hill, New York, 1999). Extracellular matrix components have a major role in the wound healing process. Collagen is the primary component. Of the 19 forms of collagen described, five subtypes are the most common (collagen I, II, m, IV, V) and present in all soft tissues, tendons, ligaments and bone (Cohen et al. Surgery: Scientific Principles and Practice, chap 3. Philadelphia, J B Lippincott, 1993, Ehrlich et al., Clin. Biol. Res., 266:243, 1988). In addition to collagen the extracellular matrix also contains glycosaminoglycans, fibronectin, laminin, fibrillins, elastin, and others. Collagen and elastin bundle orientation differs between the papillary dermis and the reticular dermis. Collagen bundle orientation is random in the papillary dermis, but perpendicular to the lines of tension in the deeper reticular dermis. Similarly, elastin fibers are sparse and fine in the papillary dermis, whereas they are thicker and form a complex three-dimensional array in the reticular dermis. The dermal vasculature forms a distinct plexus in the papillary dermis. This plexus configuration plays an important role in the remodelling process, since collagen deposition tends to occur along the pathways of neovascularization. If the plexus is absent, collagen remodelling occurs along the pathways of an altered vasculature pattern, as found in granulation tissue and scar formation.

Collagen produced is also degraded during the remodeling phase of wound healing by the action of enzymes produced again by several cell types (Agren Ms et al: J Invest Dermatol 99:709, 1992). Although collagen is the most important component for the extracellular matrix, other matrix components, act as a sequester and releaser of cytokines.

Contraction and epithelialization are closure mechanisms of wound healing. Contraction is one of the most powerful mechanical forces in the body, bringing the skin margins of the wound together until they meet, closing the wound. However, in many cases the normal contraction mechanism may result in an abnormal fixed deformity causing a functional disability. This occurs in cases where redundant skin is not available for healing, as in burns over flexor joints surfaces, such as the neck. The precise mechanisms responsible for wound contraction are not fully understood. It is also understood that extracellular matrix components have a role in wound contraction as well (Conrad P A et al: J Cell Biolo 120:1381, 1993, Desmouliere A: Cell Biol Int 19; 471, 1995)

The epidermis is the outer layer of the skin and acts as a protective film against fluid loss, pathogens, trauma and other insults. The thickness of the epidermis is maintained at a constant level by continuous exchange of keratinocytes from the basal layer to the surface where they lose the nucleus, keratinized, die and desquamate. Partial-thickness wounds heal by epithelialization due to keratinocyte migration and mitosis. Once the epidermis has been damaged a blood clot is formed, dries and forms the scab that covers the dermis protecting it. Cells from the margins of the wounds, undamaged lower layers, dermal sebaceous glands and hair follicles start to migrate to the wounded site and accelerated cell division occurs. The more superficial the wound the faster cell migration occurs. Cytokines, such as PDGF, EGF, TGF-alpha and others, are involved in inducing this response (Adzick, N. S., in Sabinston's Textbook of Surgery, $15^{th}$ Edition. pg 207, W B Saunders, Philadelphia, 1997).

Chronic wounds remain as one of the most expensive and unsolved problems in medicine. Usually chronic wounds, such as pressure, diabetic, venous stasis/ischemic ulcers, fail to heal because of a co-existing underlying health problem, such as diabetes or varicose veins. Chronic wounds heal to a point and then the healing process is arrested due to unknown causes, only to be resumed when the underlying medical condition is satisfactorily treated. Chronic wounds are the result of an extended duration of physical and biochemical insult to the tissue, in which a prolonged inflammatory stage causes further tissue damage. Polymorphonuclear leukocytes release a series of proteolytic enzymes in an effort to clean the necrotic tissue, preventing the normal release of cytokines and action of cells.

Depending on the type of the chronic wound, healing mechanisms can involve contraction (reducing the wound surface) with little need for epithelization for pressure or diabetic ulcers, to just the opposite for venous/ischemic ulcers. Either type of ulcer will close as a consequence of the treatment if the underlying cause is treated along with some general local measurements, such as infection control of the bacterial count in the wound by frequent cleaning of the wound, use of topical antibiotics and proper dressings, the surgical debridement of necrotic tissue, proper oxygenation of the area, as well as other systemic measurements, such as proper nutrition.

A system to stage pressure ulcers has been developed in an attempt to focus on the best treatment possible (dressing type to debridement requirements, etc.). The stages vary from Stage I (pre-ulcer skin damage with intact skin) to Stage 1V (full thickness skin loss with extensive tissue necrosis and muscular, tendon, or even bone damage).

A number of wound care treatments are in use. Multiple approaches have been used to replace wounds, lost, damaged, or diseased tissues. These include several types of mechanical closures (staples, sutures and adhesive tape stripes) for the primary closure of acute surgical clean wounds. Delayed primary closure wounds and chronic wounds (pressure, diabetic, venous stasis, and ischemic ulcers) require more complicated measurements since severe tissue disarrangement and loss occurs at the level of the dermis (reticular and papillary) and basal membrane complex. In recent years the availability of innumerable types of dressings, that are expensive and only marginally effective, has dramatically increased.

Several biomedical products (synthetic, biosynthetic constructs and cross-linked biologicals), are incorporated into different types of dressings or occlusive films of creams, gels, foams or injectables, in an attempt to accelerate the healing process by different mechanisms ranging from wound moisture and cytokine delivery to enhancement of cell migration or blood supply. Based upon a number of parameters such as, the location of the wound, amount and character of wound drainage, the stage and grade of wound involvement, wound depth, the involvement of adjacent structures, the presence of odor, necrotic tissue, and clean granulating tissue, a clinician will choose a dressing that will meet the needs of the particular wound environment (Choate C S; J Am Podiatr Med Assoc 84:463, 1994, Barr J E et al: Ostomy Wound Management 41:28, 1995)

For acute or chronic partial or full-thickness wounds and stage I to IV pressure ulcers with minimal exudate, there is a need for tissue debridement. A number of dressings have been used including polyurethane or copolymers films that mimic skin performance and water vapor permeability (Op-site, Bioclusive™). Others, such as Duoderm™ hydrocolloids (colloidal particles), Vigilon™ hydrogels (water), Cutinova Hydro™ hydroactives (pectin) or Aquaphor-gauze™ impregnates made of colloidal particles deliver moisture to the wound, debride necrotic tissue by autolysis, promote granulation and reepithelialization, and absorb fluids (Sefton M. et al., J Cutan Med Surg. 3 Suppl 1, 1998)

For acute or chronic partial or full-thickness wounds, stage I to V pressure ulcers with large amounts of exudate require efficient absorption and large tissue debridement. For this type of wound, the following types of dressings have been used: hydrophilic or hydrophobic foams made of polyurethane, e.g. Lyfoam™, Polymen™, Bard™ absorptive dressing or Duoderm™ granules, which are absorptive powders and pastes made of starch or copolymers that can absorb up to 100 times their weight. Other dressings, such as, Sorbsan™ is composed from fibers of calcium alginate and Carra-Sorb™ is composed of activated charcoal with silver cloth.

Topical products used in human wound care are made from animal collagen (avian or bovine collagen). Collagens are available in pastes, sheets, granules, powders, and gel forms. They are placed directly into the wound bed and require a cover dressing. Such animal collagen products are thought to stimulate a wound bed to produce its own collagen matrix.

Collagen has the ability to absorb wound fluid and break down into amino acids within the wound bed. Persons sensitive to chicken or cow by-products should not use these collagen preparations.

Healing through the release of tissue growth factors has been tried. TGF-beta, which promotes adhesion and spreading of dermal fibroblasts, is attached to a solid support (nylon mesh) that is applied to the wound (U.S. Pat. No. 5,140,200). Procuren™, an autologous platelet derived factor (PDF) dressing, or the use of fibrin in acute and chronic wounds as a vehicle to deliver other natural required factors that promote cell growth and proliferation, have shown potential.

A different approach to replacing lost dermis is the use of a synthetic or biosynthetic graft. Allografts of cadaver skin, foreskin and cross-linked porcine skin have been used as temporary wound dressings, but cannot provide a permanent dermal replacement, since they are either rejected or do not revascularize, respectively. Dermagraft™, and Dermagraft™ Transitional Dressing™ (Advanced Tissue Technologies) are made from human foreskin placed in a woven sheet of degradable material; Graftskin™ or Apligraf™ (Organogenesis) is made from a combination of human foreskin cells with bovine collagen to create a gel matrix; Epicel™ (BioSurface) or EpiDerm™ (MatTek) is made from a culture of homologous or heterologous epidermal skin cells that places only the outer most layer of the skin, but not the dermis portion. In an attempt to avoid host rejection, AlloDerm® removes the cell components of the dermis which are the major cause of the rejection response, maintaining the ultrastructural integrity of the extracellular matrix, which, if damaged, would induce an inflammatory response. (Travis J., Sci News. 155, No 25:396, 1999).

The present invention includes the following preferred methodologies and compositions for the repair and/or augmentation of acute, chronic, partial or full-thickness wounds, skin burns, pressure sore and ulcers with intended primary, delayed primary, spontaneous or secondary wounds closures. Placement into the wound bed, margin or subjacent to the wound area (fascial, subcutaneous, dermal areas) or directly into a "pocket" created in the region to be repaired or augmented (1) by injection of autologously cultured fibroblasts and/or cultured fibroblast-produced extracellular matrix such as dermal and/or fascial fibroblasts and/or lamina propria and/or and/or fascial fibroblasts and/or stromal fibroblasts and/or myofibroblasts; or (2) by the surgical engraftment of "strands" derived from the aforementioned autologous fibroblasts and/or associated extracellular matrix which are cultured in such a manner as to form a three-dimensional "tissue-like" structure similar to that which is found in vivo.

Moreover, the present invention also differs on a two-dimensional level in that "true" autologous culture and preparation of the cells is performed by the preferred embodiment that utilizes the patient's own cells and serum for in vitro culture.

Accordingly, the invention provides for an autologous (free of patient's allergic reactions) and less expensive alternative to improve and accelerate acute, chronic, partial or full-thickness wounds with intended primary, delayed primary, spontaneous or secondary wounds closures.

E. Augmentation and/or Repair of Breast Tissue Deficiencies

There are two general types of breast prosthesis. Material such as ivory, glass and paraffin were used for external contour enhancement of the breast since the sixteenth century. Currently, an external prosthesis is worn in some type of brassiere arrangement (U.S. Pat. Nos. 3,600,718; 3,665,520; 3,911,503; and 4,172,298). Surgical implantation of a prostheses is in general, made of silicone elastomer shells and fillers of silicone gels, saline, or both gel and saline mixed in single or multiple lumens. The implant may be surgically placed subcutaneous, submammary, subglandular, above the chest wall muscles, submuscular or subpectoral (Bondurant et al., Safety of Silicone Implants. Institute of Medicine National Academy Press, Washington D.C., 1999). Multiple materials have been injected to enlarge the breasts, including human tissues such as fat harvested from the same patient to be injected. Fat implantations into breast have shown poor results due to reabsorption and calcification.

Silicone usage dates back to post World War II, when Japanese barwomen started to use injections of industrial-grade liquid silicone. Despite reports of silicone's migration to other parts of the body, formation of granulomas (hard lumps), blood clots to the lungs, infections, cancer and death, the technique was adopted by American women. As an alternative to injection, the first breasts implants in the 1950's, consisted of an outer sack made of polyurethane foam or silicone and filled with saline. (Stauber et al., at PR Watch web page:http//www.prwatch.org/Q1-96/silicone.html, 1996). In 1964, a joint venture between two plastic surgeons and Dow Corning Corp developed an implant based on an envelope of silicone elastomer (a rubber-like elastic substance) filled with silicone gel. From 1965 to late 1992, seven manufacturers in the U.S. produced and sold this sole type of breast implant regionally and overseas, (U.S. Pat. Nos. 4,100, 627 and 4,790,848; European Patent Nos. 0416846AA2 and 0416846AA3).

By 1985, some 1.3 million breast implants for reconstructive as well as cosmetic indications had been completed in the U.S. Complications after surgery have been reported (Randal, J., Lancet 339:8800, 1992, Goldsmith, M., JAMA, 267 (18), 1992). Painful hardening of the breasts due to formation of fibrous scar tissue occurs around the implants. Seepage of silicone gel into the body after implant rupture (95% incidence after 17 years of use) can generate a host of immune-system disorders that are painful, debilitating and untreatable, such as rheumatoid arthritis, scleroderma, and lupus like syndromes, among other nonspecific connective tissue disorders (Angell, M.; N. Engl. J. Med., 330 (24), 1994, Gabriel et al.; N. Engl. J. Med., 330 (24), 1994, Bignall, J., Lancet., 343: 8891, 1994). Breast implants can cause a loss of sensitivity around the nipple or even a more extensive area after surgery (Woodruff, V.; Working Woman, 19 (2); 1994). Breast implants can obscure cancer growths by manual exam and/or mammography. The FDA has now removed the implants from the market until further review of cases is performed and restricted their reconstructive surgery utility for mastectomy patients (Kessler et al., JAMA 270 (21), 1993). In 1996, the FDA started its own clinical trial to assess the short-term risks of breast implants, such as rupture or hardening of the breasts (Nemecek S., Sci Amer, April, 1996)

Attempts to overcome some of the complications include a double walled or "dual lumen" prosthesis with an absorbable outer wall and an absorbable filler material between the inner and outer walls (U.S. Pat. No. 4,298,998), or with a biocompatible filler material, such as collagen gels and saline (U.S. Pat. No. 4,772,284). U.S. Pat. No. 4,840,628 describes a prosthesis that has neither a liquid core nor a permanent enclosing membrane, but has a cast silicone gel elastomer with a homogeneous cohesive structure throughout. Some breast implants with thinner non-reactive silicone oil or non-toxic flexible plastic shells are filled with water or saline solution. Poor firmness and less natural looks often result. They do not prevent capsular contracture formation, the possibility of rupture, or deflation due to saline leakage, even in more recent models displaying a leaf valve mechanism that allows custom inflation (deters W., Can J Plast Surg, 5 (4): 241,1997). Implants manufactured with a two layered non-porous and porous outer shell made of spinning polymer fibers are not completely resistant to rupture or impermeable to silicone gel migration (U.S. Pat. No. 5,376,117). More recently, in 1995, a vegetable trygliceride-filled mammary implant has been introduced to the market claiming to pose less of an obstruction to mammography testing (International Pat. No. WO 95/25549)

Despite the numerous efforts to develop a better alternative for breast contouring the field is in the need for a natural and long-lasting product that will meet quality and safety standards.

The present invention includes the following preferred methodologies and compositions that relate to the contouring, repair and augmentation of primarily female breasts and placement of compositions into the regions that are dermal, subcutaneous, submamary, subglandular, above the chest wall muscles, submuscular or subpectoral, or injection directly into a "pocket" created in the region to be repaired or augmented by: (1) the injection of autologously cultured connective tissue fibroblasts and/or cultured fibroblast-produced extracellular matrix, such as dermal (either papillary or reticular or both) and/or fascial fibroblasts and/or stromal fibroblasts and/or pre-adipocytes or adipocytes, or (2) the surgical engraftment of "strands" derived from the aforementioned autologous cells and/or cultured fibroblast-produced extracellular matrix, which are cultured in such a manner as to form a three-dimensional "tissue-like" structure similar to that which is found in vivo.

Moreover, the present invention also differs on a two-dimensional level in that "true" autologous culture and preparation of the cells is performed by the preferred embodiment that utilizes the patient's own cells and serum for in vitro culture.

F. Augmentation and/or Repair of Urological Structures—The Urethra/Ureter Meatus Sphincter Stress urinary incontinence is defined as the involuntary loss of urine through the urethra, with or without contraction of the muscle detrusor of the bladder following physical efforts, causing increased intra-abdominal pressure due to the loss of integrity of the normal anatomical structures (urethral sphincter) that is secondary to a diversity of causes. In normal continent patients, in the erect posture, there is no descent of the bladder neck below the pelvic floor muscle, resulting in equal distribution of intra-abdominal pressure to the bladder, the bladder neck and pelvic urethra. However, in stress incontinence, this is lost due to descent of bladder and urethral structures below the pelvic floor muscle. Female urinary incontinence is a common problem and is particularly prevalent where damage to the bladder or neck of the bladder has occurred during child birth. In elderly female patients, urinary incontinence is wide spread due to the former problem exacerbated by general thinning of the mucous layers of the tissues and loss of muscular tone and its supportive effect due to menopause. In men, surgical intervention for prostate conditions may be the main cause of stress urinary incontinence. In addition, incontinence in elderly men result is often due to overflow incontinence and detrusor instability. The involuntary loss of urine is unpleasant and embarrassing and can cause other medical problems such as irritation and burning of the surrounding skin and lower urinary tract resulting in infections of diverse severity.

Incontinence can consist of several other subtypes. Urge incontinence, has the symptoms of an abrupt and uncontrollable desire to urinate. Reflex incontinence, is a variation of urge incontinence in which urination occurs without any warning. Mixed incontinence, is a combination of urge and stress urinary incontinence. Overflow incontinence, is the involuntary loss of urine resulting from an overfilled bladder without any corresponding feeling or urge to void.

Vesicoureteral reflux is the abnormal retrograde pass of urine from the bladder to the ureter through a dysfunctional, larger or abnormally shaped ureter orifice into the posterolateral walls of the bladder. The reflux is typically detected by radiography, instilling contrast media into the bladder and observing its movement into the ureter. The radiological testing is needed to classify the grade of reflux ranging from 1 to 4, depending on how far the urine refluxes back into the upper ureter, the renal pelvis or kidney parenchymal tissue. Vesicoureteral reflux is a sign of multiple problems and may be caused by a variety of congenital or acquired conditions. The most important and common complication of this condition is the frequent episodes of urinary infections commonly requiring chronic antibiotic intake and that can be severe enough to compromise kidney function.

Beside the pharmacological approach, several surgical methods are available with poor results, requiring expensive hospitalization and long recovery times. Frequently the problem is undercorrected and a second or third different surgical technique may be attempted without a permanent outcome. The surgical implantation of several devices of diverse materials has been attempted with little success. The implantations are cumbersome, difficult to place and maintain and need frequent adjustments or replacements.

Recently, non-surgical approaches have been developed with only temporary success (Walsh et al, (1998): Campbell's Urology. 7th Ed. Saunders, Philadelphia.; Smith et al. (1996): Smith's Textbook of Endourology, QMP. St. Louis, Mo.). These approaches attempt to bulk a damaged, loosened or widened urethra/ureter sphincter by expansion of the tissue with the agent. At least three of these treatments use biological materials/substances. Bovine collagen implants named Zyplast™ (deters et al., 82th Annual Meeting, American Urological Association, 1987; Frey et al., J Urol, 154:804, 1994) or Contingen™ Bard (Collagen Corporation), autologous fat (Matthews et al., J Urol, 152:819, 1994), and fibrin glue have been tried. Non-biological substances that have been tried are Teflon pastes (O'Donnell et al., Postgrad Med J 66:S44,1990; Atala et al.; J Urol, 152,641, 1994), glycerine liquid or a combination of both known as POLYTEF™ (Malizia et al., Trans Am Soc Artif Intern Organs, 30:330, 1983), Urethrin™ silicone particles, swollen hydrogels, solid polymer particles, dextranomer microspheres or Deflux System™ (Stenberg et al., J Urol, 154:800, 1995) alginate particles, liquid copolymers or a combination of more than one of these substances. Silicone micro-implants (Schulman et al., Dialogues Pediatr Urol 17:6, 1994), polyvinyl alcohol and injectable bioglass (Walker et al., J Urol 148:645, 1992) have also been tried to correct vesicoureteral reflux. Technical problems and medical complications (see below) may arise from the mentioned practices (Leonard et al., J Urol, 145:115 (1991), Henly et al., J Urol, 153:2039 (1995), Lutz et al., J Urol, 154:804 (1995), Matthews et al., J Urol, 152:819 (1994), Santarosa et al., J Urol, 151: 607 (1994), Kageyama et al., J Urol, 152:1473 (1994), McGuire et al., Urol, 43:413 (1994), Monga et al., Br J Urol, 76:156 (1995), Kaplan et al., J Urol, 138:953 (1987), Malizia et al., JAMA, 251: 3277 (1984), O'Donnell et al., J Urol, 140:1101 (1988), Politano et al., J Urol, 111:180 (1985), O'Donnell et al., Br J Urol, 293:1404, O'Donnell et al., Br J Urol, 289:5).

The use of enzymatically degraded bovine collagen (atelocollagen), see U.S. Pat. Nos. 3,949,073; 4,424,208; and 4,488,911, is known to cause severe immunological allergic reactions in some patients, with the production of antibovine antibodies in 90% of treated patients, leading into the development of long-term collagen related diseases in 1-3% of the patients. The injected bovine collagen is eventually reabsorbed, broken, metabolized or eliminated by surrounding tissues, within a variable period of weeks to months, requiring repeat injections to sustain clinical effects (Leonard et al., J Urol, 145:115, 1991). The temporary effect is also observed with injections of autologous fat, fibrin glue, Teflon, glycerin liquid or a combination of these substances. The use of alginate in combination with cultured bovine chondrocytes autografts (Atala et al., J Urol, 150:74, 1993) inherently has two potential problems, adverse immunological reactions and possible calcification of the chondrocytes. The combination of alginate with bladder muscle has also been proposed to treat vesicoureteral reflux.

Side-effects of non-biological materials have been observed as local and systemic inflammatory reactions, formation of scar tissue around the site of injection, and rampant and frequent distant, unpredictable migration to the body that may cause life-threatening embolisms. The migration of materials from the site of injection may account for the temporary span of the treatment. Beside undercorrection, the production of urinary retention due to complete urethral closure by overcorrection has been reported.

Accordingly, a non-surgical approach utilizing autologous biological substances to repair/augment defective urethral/ureter sphincters with a long-lasting correction of the urological problem without side effects is needed.

The present invention includes the following preferred methodologies and compositions for the repair and/or augmentation of urinary stress and other types of incontinence (mixed, overflow) and/or vesicoureteral reflux by reforming or repairing the tissue "a sphincter structure" surrounding the urethra and ureters, causing a reduction in the abnormally wide and loose lumens. This can be accomplished by placement of compositions into the regions surrounding the urethra and ureters or directly into a "pocket" created in the region to be repaired or augmented by (1) the injection of autologously cultured fibroblasts or cells and/or cultured fibroblast-produced extracellular matrix, such as dermal and/or fascial fibroblasts and/or lamina propria fibroblasts and/or stromal and/or pre-adipocytes or adipocytes, or (2) the surgical engraftment of "strands" derived from the aforementioned autologous fibroblasts and cells and/or cultured fibroblast-produced extracellular matrix, which are cultured in such a manner as to form a three-dimensional "tissue-like" structure similar to that which is found in vivo. This type of engraftment should be especially useful for as a better alternative to Pubovaginal slings or other tissues traditionally used for the procedure (e.g. fascia lata, rectus fascia, vaginal wall, round ligament etc) for the treatment of urinary incontinence in women with stress urinary incontinence due to Intrinsic Sphincter Deficiency (ISD) in the presence of urethral hypermotility.

Moreover, the present invention also differs on a two-dimensional level in that "true" autologous culture and preparation of the cells is performed by the preferred embodiment that utilizes the patient's own cells and serum for in vitro culture.

G. Augmentation and/or Repair of Periodontal Disease and Disorders

Preprosthetic techniques in dentistry refer to the procedures that need to be performed in order to obtain a healthy periodontal complex capable of withstanding the stresses of mastication, tooth brushing, trauma from foreign objects for tooth preparation associated with implants (crowns, bridge, partial or complete dentures), rehabilitation procedures after oral, maxillary or mandibular cancer and tumor resections, post-periodontal disease (gum disease or pyorrhea) treatments or after physical trauma or reconstructive procedures for congenital cleft palate/lip. Healthy gum tissue and bone form the supportive foundation of each tooth. These techniques are also used when the presence of mucogingival or alveolar ridge problems are present, as well as when bone protection and preservation or root coverage by means of gum augmentation have to be achieved (Cohen E. S.; Atlas of Periodontal Surgery. Lea & Febinger. Philadelphia, 1988; Fonseca & Davis.; Reconstructive Preprosthetic Oral and Maxillofacial Surgery ed., W. B. Saunders, Philadelphia, 1995).

Soft and hard tissue reconstruction techniques were first conceived and designed when the only options were conventional dentures. However the principles of the techniques are easily adapted and widely used in situations that require soft or hard tissue modifications when implant related prostheses are employed or in any of the health situations mentioned above. The main goals to achieve when dental restoration is attempted are to provide stable soft and hard tissues upon which dentures or implants can rest or be placed and the deepening of the flange area so that increase resistance to displacement forces is provided.

Soft tissue procedures using grafts date back to 1894 when the first Thiersch graft (thin-split thickness graft) to a granulating defect of the buccal mucosa was performed (Slanetz., et al, Am J Surg, 104:721, 1962). The first peri-oral skin graft was performed in 1916 (Kilner T. P, et al,: Br J Surg, 9:148, 1921). There are five general groups of soft tissue procedures or combination of soft and bone tissues applications. 1) Mucogingival surgery uses full-thickness, partial-full thickness and partial-thickness periodontal flaps or free soft tissue/gingival autograft, ridge augmentation or sub-epithelial connective graft from tissue obtained primarily from the gingival zone of the palate. Full-thickness soft or connective tissue grafts or more recently, hydroxyapatite implants, are used for alveolar ridge augmentation; 2) Mandibular soft tissue procedures are mainly used for the adaptation of complete/partial dentures in the edentulous atrophic ridge. Vestibuloplasty lowers the floor of the mouth with skin grafts, while anterior vestibuloplasty utilize free mucosal graft (from palate, labial, cheek mucosa); 3) Maxillary soft tissue procedures are used for the adaptation of complete/partial dentures in the edentulous atrophic ridge with vestibuloplasty skin grafts, palatal mucosal flaps, or buccal inlay vestibuloplasty, considered only when there is an absolute deficiency of facial mucosa, due to trauma or ablative surgery; 4) Mandibular or maxillary augmentation with simultaneous vestibuloplasty (several types), is used for patients with simultaneous bone loss. These procedures use either hydroxyapatite particles or bone grafts (autogenous, allogenic from bank, composite). (Cohen E. S.; Atlas of Periodontal Surgery. Lea & Febinger. Philadelphia, 1988; Fonseca & Davis.; Reconstructive Preprosthetic Oral and Maxillofacial Surgery edition. W.B. Saunders, Philadelphia, 1995).

These surgical techniques and procedures that work well for most patients have disadvantages and complications. In any type of graft there are two operative sites, potential infection complications, scar formation from the skin donor site, discomfort, compromised blood supply for the graft site with subsequent necrosis, reabsorption or retention of the graft, potential hemostasis problems, poor aesthetic results (color and texture differences) and with skin, a particular problem exists which is the presence of hair follicles in the graft. Many procedures require several weeks to months before the soft tissues are ready for prosthetic or implant adaptation causing great discomfort to the patient. Recently, and whenever bone rehabilitation is involved, biomaterials have been tried. Xenogenic hydroxyapatite obtained from bovine (Callan D. P.; et al. J Periodontol, 64-575 1993) still remains as a good option. For soft tissue grafting and augmentation, fabricated cultured mucosal epithelium (Ueda M.; et al. Oral Surg Oral Med Oral Pathol Oral Radiol Endod, 86-393 1998 and Tsai C.; et al. J Craniomaxillofac Sur, 254, 1997) has proved to be an acceptable peri-implant material. Allograft gingival connective tissue grafts have been reported to restore the gums and mucosal layer (Duarte C.; et al. J Esthet Dent, 8-269, 1996).

Periodontal (gum) diseases are the major cause of tooth loss in the adult population. Periodontal diseases are caused by bacterial infections that attack gums, ligaments and bone. Often painless, these diseases develop slowly or progress quite rapidly, causing major damage to the periodontal complex. Bacteria around the teeth forms plaque, that hardens with time to form tartar or calculus that can only be removed by professional cleaning. If not removed this condition creates chronic infection and inflammation in and under the gum line.

The chronic inflammation process leads to the formation of pockets (spaces of more than 3 mm) that develop in the normal sulcus (groove) between the gum and the tooth. As this space increases in depth, the root of the tooth gets exposed, the ligaments and bone get involved and the tooth is no longer stable, becoming loose in its socket. After the diagnosis is done and depending upon the severity of the disease, treatment begins with cleaning that usually includes scaling to remove plaque and tartar. The tooth roots may also be planed to smooth the root surface, allowing the gum to heal and reattach to the tooth. In the presence of large pockets (>5 mm) the cleaning process may not be enough. Surgical lifting of the gums to further expose and clean the root of the tooth may be required. If extensive gum tissue and/or bone have been lost, grafts are then required. (American Dental Association.: Periodontal Diseases, 1996)

The present invention includes the following preferred methodologies and compositions for preprostethic/periodontal minor and major soft tissue repair and/or augmentation replacing mucosal or connective tissue flaps and grafts. The inventions can be accomplished by placement of compositions into the various layers of the connective tissue regions (e.g., lamina propria of the gum gingival for gum recession or pyorrhea) surrounding the above areas for repair and augmentation or directly into a "pocket" created in the region to be repaired or augmented by (1) the injection of autologously cultured fibroblasts or cells and/or cultured fibroblast-produced extracellular matrix, such as dermal and/or fascial fibroblasts and/or lamina propria fibroblasts and/or pre-adipocytes or adipocytes, or (2) the surgical engraftment of "strands" derived from the aforementioned autologous fibroblasts or cells and/or cultured fibroblast-produced extracellular matrix, which are cultured in such a manner as to form a three-dimensional "tissue-like" structure similar to that which is found in vivo.

Moreover, the present invention also differs on a two-dimensional level in that "true" autologous culture and preparation of the cells is performed by the preferred embodiment that utilizes the patient's own cells and serum for in vitro culture.

H. Augmentation and/or Repair of Hernias

A hernia is a protrusion through the tissues normally containing it. A powerful muscular effort or strain occasioned by lifting a heavy weight, or any condition which raises intra-abdominal pressure may lead to a hernia. Hernias can also be congenital in origin. The most common cause of a hernia occurs when abdominal structures protrude through an abdominal wall defect (weakness, tear or opening). A hiatal hernia occurs internally when a portion of the stomach pushes through the diaphragm that separates the chest from the abdomen. Among the abdominal hernias, umbilical, femoral or the inguinal ("groin"), the inguinal hernia is the most prevalent, occurring in 3-4% of the normal male population. Therefore hernias are a common ailment with approximately over a half million Americans undergoing surgery for its treatment annually (Schwartz et at., Principles of Surgery, 7th Ed., McGraw-Hill. New York, 1999). As a rule, a hernia consists of three parts—the sac, the coverings of the sac, and the contents of the sac. The sac is formed from the peritoneum, the coverings are derived from the layers of the abdominal wall through which the sac passes and the contents can be almost any abdominal viscous, except for the liver. The most common contents are fluid (peritoneal), omentum, intestine, portions of the bladder, a diverticulum of the bladder, ovary (with or without fallopian tube) and Meckers diverticulum (Mann et al., Bailey & Love's Short Practice of Surgery, $22^{nd}$ Ed., Chapman & Hall Medical, London., 1995).

Hernias may not cause severe symptoms, especially if they are small and reducible (when the contents of the sac can be returned to their normal position). The discomfort or pain may increase, however with physical activity and the hernia may increase in size. If untreated, several complications may arise. The most severe and common is strangulation. Strangulation occurs when the blood supply to the intestine contained in the hernial sac is compromised and necrosis (gangrene) of the involved intestinal loop sets in, requiring immediate surgical intervention. Strangulation occurs in up to 3% of groin hernias and mostly at the extreme periods of the lifespan. Another severe complication is the ripping of the abdominal content, (incarceration) within the hernia, requiring emergency surgical release.

Inguinal (groin) hernias are divided into direct and indirect according to some anatomical characteristics. In a direct hernia, the sac protrudes outward and forward through a defect in the posterior wall of the inguinal canal (fascia of the transversalis muscle), between the deep epigastric artery and the end of the rectus muscle. In an indirect hernia, the sac passes through the internal inguinal ring and the inguinal canal, traveling alongside the spermatic cord, obliquely or indirectly toward and ultimately into the scrotum becoming a scrotal hernia. Under standard circumstances, the repair of a hernia requires surgical intervention. Currently, however, more efficient and less invasive techniques, including controversial laparoscopic repair are becoming popular. Often the procedures are performed on an outpatient basis, with local or regional anesthesia and requiring less recovery time. In general, the surgical repairment of the inguinal hernias consists of three 3 stages: 1) excision of the hernial sac, 2) repair of the stretched internal inguinal ring and the transversalis fascia (indirect hernia), and 3) further reinforcement of the posterior wall of the inguinal canal. Stages 2 and 3 must be achieved without tension. Fascial flaps, or synthetic mesh implants are employed when the deficiency of the posterior wall is extensive.

In the last decade of the nineteenth century, rapid advances in the knowledge of anatomy, surgical antisepsis, and anesthesia has led to surgical treatments of hernias. Different methods of "layer closure" were devised during this period by European and American surgeons. The techniques developed by these pioneers have been applied without significant alteration or improvements, for the last 100 years, carrying a recurrence risk between 10 and 12%. Recurrence risks were dramatically reduced to 1.5 to 2% of certain types of hernias when the modification of a "layer closure" technique using the transversalis fascia in an overlapping fashion was introduced by surgeon Dr. E. E. Shouldice in 1940 (Shearburn, E. W et al.; Surg, 66:450, 1969 and Glassow, F.; Hernia, Second Edition. Philadelphia, J. B. Lippincott Company, 1978).

During the 1970's, Dr. Usher pioneered the use of polypropylene mesh for the repair of abdominal wall hernias and opened a field for the use of non-degradable and biologic-tolerant synthetic prosthesis materials in the correction of hernias claiming a recurrence rate of 0.4% (Usher, F. C Surg. Gynecol. Obstet., 131:525, 1970).

Other treatments in use for a hernia consist of several "tension free" techniques. The simplest technique is the ambulatory procedure under local anesthesia in which a small incision is made over the site of the hernia. The peritoneal bulge is returned to its normal location, and the repair is achieved by placing a piece of mesh at the opening in the tissue. This is firmly held in place by intra-abdominal pressure and the outer incision is then closed. More complicated "tension tree" techniques require the mesh to be secured in place by suturing its superior edge to the internal oblique muscle.

The prosthesis used is made of polypropylene and polyester. This type of mesh desirably incites a prompt fibroblast response and is rapidly integrated in the body with minimal inflammation after 3 to 4 weeks. Complications due to adhesions, intestinal obstruction and fistulization have been reported when not enough care is exercised to prevent the abdominal viscera from contact with the mesh directly.

The "Tension Free" technique as originally described, called for the implantation of the prosthesis as a mesh, patch or plug, in combination with a surgical technique that repairs the hernia without pulling muscle together under tension. Several "Tension Free" techniques are now used. One of the simplest is an ambulatory procedure under local anesthesia in which a small incision is made over the site of the hernia. The peritoneal bulge is returned to its normal location, and the repair is achieved by placing a piece of mesh at the opening in the tissue. This is firmly held in place by intra-abdominal pressure while the outer incision is closed. More complicated "Tension Free" techniques secure the mesh in place by suturing its superior edge to the internal oblique muscle.

Several combined techniques use traditional products called Marlex™, Davol™, Prolene™, or Surgipro™, that are made from knitted or braided monofilaments or strands of polypropylene; or Mersilene™, that is made from fibers of polyester Dacron; or Gore-Tex™, that is made from expanded polytetrafluoroethylene, e.g., PTFE or Teflon. These prostheses have replaced, for all practical purposes, the inconvenient grafts of fascia lata.

The most common and severe complications arising from the use of a mesh is infection, since all the synthetic materials can become sequestered, act like a foreign body, aggravating and prolonging infections. Adhesions, intestinal obstruction and fistulization have been reported when not enough care is exercised in preventing the abdominal viscera from contact with the mesh directly. (Schwartz et al., Principles of Surgery, $7^{th}$ Ed., McGraw-Hill. New York, 1999).

The present invention uses the following preferred methodologies and compositions for the repair and augmentation of the various types of hernia. The invention is accomplished by placement of the compositions consisting of autologously cultured fibroblasts and/or cultured fibroblast-produced extracellular matrix, such as dermal and/or fascial fibroblasts and/or stromal fibroblasts. (1) in a preferred methodology utilized to repair an abdominal wall defect, the placement of "strands" derived from the aforementioned autologous cultured fibroblasts and/or cultured fibroblast-produced extracellular matrix, which are cultured in such manner as to form a three-dimensional "tissue-like" structure similar to a prosthetic mesh or plug is used, or (2) the combination of a routine "tension free" technique with the insertion of a prosthetic mesh in tandem with the injection of the aforementioned autologous cultured fibroblasts and/or cultured fibroblast-produced extracellular matrix, preferably the placement of fascial fibroblasts around the mesh to promote an immediate fibroblastic response resulting in a faster incorporation of the prosthesis, or (3) the combination of one of the traditional surgical methods that stitch together the sides of the defect in conjunction with the injection of the autologous cultured fibroblasts and/or cultured fibroblast-produced extracellular matrix, or (4) implantation of fascial flaps made of autologous fascial fibroblasts and/or cultured fascial fibroblast-produced extracellular matrix, or (5) fascial flaps made of the autologous fascial fibroblasts and/or cultured fibroblast-produced extracellular matrix to replace mesh implants, to be used for layer closure techniques or to be used to suture into the fascial layers of the herniated tissues and muscle for closure of the hernia, or (6) the injection of the autologous cultured fibroblasts and/or cultured fibroblast-produced extracellular matrix in combination with laparoscopic surgical techniques to repair the hernia.

Moreover, the present invention also differs on a two-dimensional level in that "true" autologous culture and preparation of the cells is performed by the preferred embodiment that utilizes the patient's own cells and serum for in vitro culture.

I. Augmentation and/or Repair of Gastroesophageal Reflux

Gastroesophageal reflux (GER) is one of the most common gastrointestinal ailments in the adult population and the most common esophageal disorder in childhood, especially during the neonatal period (Avery G et al.; Neonatology, Pathophysiology and Management of the Newborn. Fifth Edition. Lippincott Williams &n Wilkins, Philadelphia, 1999).

Gastric contents normally are retained within the stomach through the action of the lower esophageal sphincter, a zone of high pressure in the distal esophagus that remains tonically contracted except during deglutition. When this sphincter is functionally incompetent, intermittently relaxed or disrupted, GER occurs.

As gastric contents reach the esophagus, a feeling of warm fluid climbing the throat along with heartburn is defined as a burning retrosternal discomfort, and is the characteristic symptom of GER. Regurgitation is defined as the effortless appearance of gastric or esophageal contents in the mouth, and when bitter-taste or sour, it is associated with severe GER due to the incompetence of both upper and lower esophageal sphincters (Wilson J et al.; Harrison's Principles of Internal Medicine. Fourteenth Edition, Mc Graw Hill, New York, 1997). An undesirable consequence of GER is esophagitis, the chronic inflammation of the superficial squamous mucosa or of the distal esophagus, causing erosion and ulcers due to contact with acid and pepsin from the stomach. If the problem persists uncorrected, the squamous epithelium may be progressively replaced with metaplastic gastric-like epithelium more resistant to acidic fluids and this epithelium is more prone to malignant transformation into esophageal cancer. In newborns and infants, and in the adult population, GER causes the recurrent aspiration of food contents into the trachea, bronchi and lungs causing apnea, bradycardia, pneumonitis or exacerbation of pre-existing pulmonary disease. Another important problem related to GER in newborns and infants is the failure to thrive caused by the regurgitation or reflux of considerable amounts of formula after feedings (Avery G et al.; Neonatology, Pathophysiology and Management of the Newborn, Fifth Edition. Lippincott Williams & Wilkins, Philadelphia, 1999). GER may exist as a primary disorder due to true sphincter incompetence or intermittent relaxation. Secondary GER may be a manifestation of another gastrointestinal problem, such as congenital tracheo-oesophageal fistula or esophageal atresia or to transient incompetence of the sphincter, which is especially true for newborns and infants. GER is a virtual certainty after surgery to correct tracheoesophageal fistula or esophageal atresia, due to severe incompetence of the sphincter. These patients may need aggressive GER treatments to prevent long-term complications from chronic esophagitis, as stricture formations may cause stenosis.

Current goals of treatment to decrease GER are to neutralize refluxate, improve esophageal clearance and protect the esophageal mucosa (Wilson J et al.; Harrison's Principles of Internal Medicine. Fourteenth Edition, Mc Graw Hill, New York, 1997). Standard treatments to reach these goals use basic general measures in uncomplicated cases. Examples of these measures are the elevation of the head of the bed during resting or sleeping, control of bodyweight, or avoidance of foods with substances that are known to increase abdominal pressure (fatty foods, coffee, tea, colas, orange juice, chocolate, mint, as well drinking large amounts of fluids with meals), alcohol and smoking. Drug treatments include drugs to inhibit gastric acid secretion known as H2-receptors antagonists or hydrogen pump antagonists.

GER may be treated successfully with stronger measures, such as with surgery. Surgical fundoplication in approximately 95% successful in the cases among infants and younger children. The most common surgical procedures for young children and infants employ the Nissen and Thal fundoplications in which the stomach is wrapped around the distal portion of the esophagus. Recently, procedures using laparoscopy have been employed. The decision to treat adults with surgery has to be carefully considered, since the procedures have a much lower rate of success (Schwartz S et al.; Principles of Surgery. Seventh Edition. Mc Graw-Hill. New York, 1999).

The present invention includes the following preferred methodologies and compositions for the repair and/or augmentation or bulking of the esophageal sphincters through the operative endoscope by placement of said compositions by (1) the injection of autologously cultured fibroblasts and/or cultured fibroblast-produced extracellular matrix such as dermal and/or fascial fibroblasts and/or lamina propria and/or and/or fascial fibroblasts and/or lamina propria fibroblasts and/or adipocyte or pre-adipocytes into various layers of the esophagus (muscularis mucosae, and/or areolar or submucosa), or injection directly into a "pocket" (e.g. cutting of the connective tissue strands between the mucous and the muscular layers, created in the region to be repaired or augmented), or (2) the surgical engraftment of "strands" derived from the aforementioned autologous fibroblasts and/or cultured fibroblast-produced extracellular matrix, such as dermal and/or fascial fibroblasts, and/or lamina propria fibroblasts and/or adipocytes or pre-adipocytes, which are cultured in such a manner as to form a three-dimensional "tissue-like" structure similar to that which is found in vivo.

Moreover, the present invention also differs on a two-dimensional level in that "true" autologous culture and preparation of the cells is performed by the preferred embodiment that utilizes the patient's own cells and serum for in vitro culture.

J. Augmentation and/or Repair of Tendons and Ligaments

Tendons and ligaments are dense complex macromolecular networks of connective tissue structures organized in parallel fiber bundles of different types of collagen (~90% of fibrillar collagen type I, less than 10% being collagen type III and traces of other types of collagen) containing large amounts of water (making for ⅔ of their weight). Tendons anchor the muscles to bones or into the joints (Kerr J: Atlas of Functional Histology. Mosby. London, 1999 and Duthie R. et al., Mercer's Orthopedic Surgery. Ninth Edition. Arnold. London, 1996). Ligaments keep together the different bony or cartilaginous structures of a joint providing stability and mobility to it. Muscles, tendons, ligaments and bones comprise units, and an injury to one component of the unit affects it as a whole.

Ligaments and tendons are commonly injured during athletic activity and due to the fact that that sports are an increasingly important part of day to day life in the U.S, the number of ligament and tendon injuries have steadily increased over the past few decades. Ligaments and tendons of the knee (anterior cruciate, posterior cruciate and collaterals), ankle (deltoid, inferior tibiofibular and laterals) and shoulder (rotator cuff among others) are the most frequently injured, since these structures sustain the major strain during repetitive physical activity. However, almost any ligament or tendon in the human body can be injured, torn or ruptured.

Injuries of the muscle-tendon complex can be classified according to the severity in three types (Canale S.: Campbell's Operative Orthopaedics. Ninth Edition. Mosby, St Louis, 1998):

1—Mild strain (grade I)—Slightly pulled muscle without tearing of muscle or tendon fibers. There is not loss of strength.
2—Moderate (grade II)—Tearing of fibers in a muscle, tendon, or attachment to bone. Strength is diminished.
3—Severe (grade III)—Rupture of the muscle-tendon-bone attachment with separation of fibers.

The anterior cruciate ligament (ACL) of the knee is the most commonly injured ligament of the human body accounting for more than 100,000 reported injuries per year in the U.S and 150,000 surgical procedures to treat them (Menetrey J. et al., Tiss Engin. 5, 435,1999 Lin V. et al., Tiss Engin. 5, 443,1999). As the most common ligament injury, it serves as a perfect sample to illustrate the healing problems, surgical alternatives to repair or the complete reconstruction with the pitfalls and complications that are common to all ligaments.

The ACL attaches to the femur on one end and to the tibia on the other. The ACL is one of the four ligaments that are critical to the stability of the knee joint, preventing it from sliding too far forward and giving stability during angulation and rotation movements. ACL injuries are troublesome because they take a long time to heal and often healing very poorly (Lin V. et al., Tiss Engin. 5, 443, 1999, Canale S.: Campbell's Operative Orthopaedics. Ninth Edition. Mosby, St Louis, 1998 and O'Donague D. et al., J. Bone Joint Surg.

[Am.] 48, 503, 1996). This is a problem common to all ligaments. Surgical procedures have to be delayed until the initial symptoms subside, the surgical procedures are far from ideal, often turning out to be futile, and the post-operative period is long, requiring intensive rehabilitation.

Surgical options for the ACL ligament reconstruction use a portion of another ligament, the patellar being the most common option (the patellar ligament connects the kneecap to the tibia). This autograft alternative is far from ideal since it can cause mechanical instability and loss of function of the site from which grafts are taken. The use of allografts (Arnoczky S., et al., J. Bone Joint Surg. 64A, 217,1982, Czitrom A. et al., Allografts in Orthopedic Practice. Williams & Wilkins, Baltimore, 1992 and Canale S.: Campbell's Operative Orthopaedics. Ninth Edition. Mosby, St Louis, 1998) of ligaments from cadavers, have the inherent problems described above, in addition to potential disease transmission of infectious agents from the donor. Furthermore, in both auto and allografts, the internal part of the grafts show necrosis shortly after surgery. This is a major reason why biological grafts do not provide adequate mechanical strength until a complete remodeling of the graft is achieved. Human studies have shown that this process, called ligamentization, can take up to 3 years to reach completion, after going through several stages of ischemic necrosis, revascularization, cell proliferation and eventually collagen remodeling (Menetrey J. et al., Tiss Engin. 5, 435.1999 and Rougraff B. et al., Am. J. Sports Med. 21,277, 1993).

In the 1970s, a synthetic prosthesis made of polymers was introduced as an alternative, but never gained total acceptance because of mechanical failure, due to fatigue and abrasive wear. The most popular models of synthetic ligaments are the Gore-Tex™ (EP 0106501 B1, EP 0260787A1, U.S. Pat. No. 5,197,983) and the Striker Dacron. The lack of long-term studies showing their performance makes it prudent to limit their use to salvage procedures in which autografts and reconstructive procedures have failed (Lin V. et al., Tiss Engin. 5, 443.1999, Canale S.: Campbell's Operative Orthopaedics. Ninth Edition. Mosby, St Louis, 1998, Durselen L. et al., Biomaterials 17, 977, 1996 and Chen E. H., et al., J. Biomed. Mater. Res. 14, 567, 1990).

Thus the therapeutic options using ligaments entirely grown in the laboratory is an outstanding alternative. The present invention includes the following methodologies and compositions for the replacement, repair, remodeling and/or augmentation of ligaments, tendons and muscles of the joints: (1) the endoscopic injection of autologously cultured fibroblasts and/or cultured fibroblast-produced extracellular matrix (either from tendon or ligament) and/or myoblasts and/or into the torn area of the ligament, tendon or muscle, respectively, or the endoscopic injection directly of the aforementioned composition of fibroblasts and/or cultured fibroblast-produced extracellular matrix into a "pocket" (e.g. cutting of the connective tissue bundles around the torn area of the ligament, tendon or muscle, creating the region to be repaired or augmented), or (2) the surgical engraftment of "strands" derived from aforementioned autologous cultured fibroblasts and/or fibroblast-produced extracellular matrix (either from ligaments or tendons or both) and/or myoblasts, which are cultured in such a manner as to form a three-dimensional "tissue-like" structure similar to that which is found in vivo. The complete replacement of the ligament by means of the use of a tissue engineering ligament is made with a biodegradable material (e.g., polylactic or polyglycolic acids) scaffold in which autologously cultured fibroblast (either from tendon or ligament) are seeded to form a bundle like tubular structure resembling the ligament to be replaced.

K. Augmentation and/or Repair of Hair Growth During Androgenetica Alopecia

Hair loss is a medical abnormality or disease that affects over 40 million men in America and a substantial amount of women as well (Geraci R.; Men's Health, June 1999). Hair loss is commonly divided into two categories, cicatricial (scarring) and non-ciacatricial alopecia. The cicatricial alopecia results from hair follicle damage complicated by various pathological changes in the surrounding skin, in which burns are a common cause. Non-cicatricial alopecia is caused by either functional or structural disorders of the hair follicle itself. This latter condition may be further divided into primary and secondary causes. Secondary follicular disorders are usually the results of chemotherapy or radiation treatments for cancer, nutritional, hormonal disorders or even stress. Alopecia areata and male pattern alopecia (androgenetica alopecia) are common primary follicular disorders, in which androgenetica alopecia (ADA) is the most common, causing refractory and mostly irreversible baldness. Their fully pathogenetic mechanisms are unknown.

Hair growth is a dynamic process involving phases or steps; each and every hair grows from an individual hair follicle, the size and length of the follicle determines the thickness and relative length of the hair. Under normal healthy conditions the normal pattern of body hair growth is generally well maintained with a balance of terminal hairs (coarse and long) and vellus hairs (thin and short). In the presence of hormonal abnormalities or changes, inflammation, toxic exposures, and stress, abnormal conditions within the follicle may occur, inducing either gradual thinning or rapid loss of the hair.

Baldness is a complex form of hair loss. It may appear as a complete loss of the hair shaft in patchy and wide scalp regions, a reduced density of terminal hair, or a replacement of terminal hairs with vellus hairs. Alopecia areata, alopecia totalis or alopecia universalis are three conditions in which there is a massive and complete loss of scalp hair, usually due to severe degenerative follicular toxic or inflammatory processes. Female alopecia is characterized by a reduced density of the terminal hairs in the vertex or frontal edge of the scalp. Male pattern baldness (androgenetica alopecia) is characterized by the thinning of scalp hairs concomitant with replacement by vellus hairs. Female and male alopecia usually lack the severe dystrophic and degenerative follicular changes of the complete alpacas, but show progressive diminution of the size of the hair follicles.

The cycle of a hair follicle undergoes through three main phases: 1) anagen, the active growing phase, 2) catagen, a transitional phase and 3) telogen, a quiescent phase (Percoraro et al., J Invest Dermatol, 43:145, 1964, Adachi et al., Curr Probl Dermatol, 5:37, 1973, Peus et al, Dermatol Clin, 14:559, 1996). The average duration of the anagen phase is 3 years. Normal replacement of old hair with new hair by cyclic turnover usually occurs without loss of hair.

Catagen is the involution phase involving autophagy (self-absorption). The induction mechanism of the catagen phase is not known. However, drugs that inhibit mitosis, such as cyclophosphamide and colchicine, or radiation, can induce the premature catagen phase. The duration of catagen can be several months.

During the resting phase, telogen, the club hair does not shed until a new hair emerges from a new anagen follicle. The duration of telogen phase varies greatly with the region of the body, sex, age, and ethnicity. In the scalp it is known that the average duration of telogen is about 100 days.

Overall the rate and cycles of growth vary from species to species and within the same animal from one part of the body to another. In man each follicle has its own growth cycle largely independent of others and this independence may be determined by genetic factors. Follicles with a longer anagen phase produce longer terminal hairs. Scalp follicles have among the longest anagen phase (3 years), thus producing the longest hairs in the human body. It is known that the average normal number of hairs in the human scalp is approximately 100,000, with a normal shed rate of 100 scalp hairs daily and growth rate of 0.3 to 0.4 mm per day (Kaufman K D.; Derm-Clin, 14:4, p697,1996).

The transformation of hair follicles from vellus to terminal takes place during the normal developmental process and under abnormal conditions (Saitoh et al., Advances in Biology of the Skin, 183, Pergamon Press, Oxford, 1969). The infant's thin hair gradually changes to thick hairs as the child gets older and this process is due to the scalp's individual follicle enlargement. However, body hair remains thin, silky and short as vellus hairs until the hormonal influence of primarily testosterone during puberty influences the secondary hair growth in both sexes and facial hair growth in males. Increased circulating levels of ovarian androgens in females show a greater amount of coarse, thick facial hair called "hirsutism", yet paradoxically, androgens induce progressive thinning and loss of scalp hair in genetcially pre-disposed men and women. Therefore, androgens can be either hyperplastic (hair growth) or hypoplastic (alopecia).

The hypoplastic effect of androgens in androgenetica alopecia (AGA) was investigated over 50 years ago by Dr. James Hamilton's (Hamilton J B.; Am J Anat, 71-451, 1942). Men deprived of testicular androgens by castration during pre-puberty exhibited no baldness and the earlier the castration of men during adolescence, the fewer cases of and less severe the case of baldness compared to adult castration, confirming the hypothesis that androgens, mainly its metabolite dihydrotestosterone (DHT), were required to cause common baldness. Independent of age, no further hair loss occurred after castration and administration of exogenous testosterone to the castrated men produced typical, progressive male pattern baldness (MPB). Individuals with scalps resistant to the effect of testosterone belong to families with virtually no cases of baldness, showing that a genetic component is important for developing androgen-induced hair loss (Kaufman K D.; Derm Clin, 14, Vol 4 p. 697, 1996). These initial observations supported the hypothesis that androgens, primarily its metabolite dihydrotestosterone (DHT), are causative agents in male pattern baldness.

Androgenetica alopecia describes a condition in which a decrease in scalp hair density is the result of a progressive, spontaneously irreversible transformation of the terminal follicle into a vellus one, with overall decrease in the size of the follicle and a reduction in the volume of the hair matrix and the dermal papilla. These follicles may eventually lose their potential for cycling by the progressive shortening of anagen phase. This regressive change of hair follicles involves no pathological, degenerative or dystrophic event, but rather is due to a genetically determined premature age-related process apparently triggered by the postpubertal elevation of serum testosterone.

The genetic mechanism(s) of androgenetica alopecia is unknown. Recently, a human gene involved in another type of hair loss (alopecia universalis) was located on chromosome 8 and encodes for a transcription factor (Ahmad W., et al: Science, Vol 279-720, Jan. 30, 1998).

There are two useful classifications of male pattern baldness. The Hamilton classification is considered more accurate, while Norwood's is more detailed and extensively used.

There are seven stages on Norwood's scale as follows. Type 1 to 2 is ranges in area from a minimal frontotemporal recession to a symmetrical triangular areas of recession. Type 3 is a deep frontotemporal, triangular, symmetrical recession extending posteriorly and is mostly bare. In the type 3 vertex, most of the hair loss occurs in the vertex, with or without deep frontotemporal recessions. In type 4, there is deep posterior frontotemporal recession and more extensive vertex loss. The line of hair that separates both bald areas is thinning and in type 5, this line of hair is even thinner, containing sparser and finer hair. In type 6, the line (bridge) of hair that crossed the crown is now gone. The frontotemporal and vertex bald areas are now confluent. In type 7, the most severe form of baldness, all that remains is a narrow horseshoe-shaped band of hair that starts laterally to the ears and extends posteriorly on the sides and low in the occipital area of the scalp.

Although the grade of hair loss and its incidence are much less than in men, approximately 25% of Caucasian females show bitemporal recession (type 1) by age 40. (Ebling et al., Textbook of Dermatology, Vol 2: 1937, Blackwell, Oxford, 1986). Thinning of the hair slowly progresses and extends to the vertex and the frontal hair line, primarily after menopause. Severe baldness is unusual in women. However, women abnormally producing higher levels of androgens from the ovaries or the adrenals often show a complete recession of hair on the frontal scalp. The Ludwig (Ludwig E., Br J Dermatol, 97:247, 1977) female alopecia classification, grades the hair loss in three stages. Grade I is the thinning and loss of crown hair, grade II is the further thinning and pronounced rare factions, and grade III is full baldness with complete denudation.

Therapeutic and cosmetic approaches have been undertaken for androgenetica alopecia. Many, if not most, do not work or are merely temporary or partial solutions, that are expensive and often are not free of possible dangerous or adverse secondary effects.

To date only two drugs are approved by the FDA for the treatment of androgenetica alopecia. Minoxidil (Rogaine™) is a vasodilator that claims to stimulate the conversion of vellus hair into terminal hair at the vertex of the scalp (U.S. Pat. No. 4,139,619). A 5% concentration applied as a topical solution is reported to regrow some fine hair in the vertex scalp region of 50% of the users after a year of constant use. As a vasodilator there are safety concerns about possible secondary adverse effects. Finesteride (Propecia™), a 5 α-non reductase type 2 inhibitor, prevents the conversion of testosterone into DHT. This agent, approved in 1997 for the oral treatment of androgenetica alopecia (U.S. Pat. Nos. 5,516,779; 4,377,584; and 4,760,071), has been reported to be effective in reducing further hair loss in 52% of the users after a year of constant use. Women in reproductive years must be careful not to have any contact with the medication because of known risk of birth defects. Recent reports indicate that the use of both compounds (minoxidil topically plus finesteride orally) might slightly increase the percentage of males regrowing some hair after one year of constant use.

Several herbal remedies that claim to help alleviate baldness are available over the counter including pygeum, saw palmetto, stinging nettles and green tea.

Surgical options to treat androgenetica alopecia/male pattern baldness range from follicular and hair transplants, to laser hair transplants, to aggressive and controversial scalp reductions, scalp flaps, or linear, round, or square hair grafts. Scalp extensions using an extender (titanium, silicone plates or balloons) placed under the scalp to stretch the bald skin for further excision is yet another surgical alternative (Unger W P K.; Derm Clin, 14, Vol 4-783, 1996). Surgical procedures require hospitalization, anesthesia and recovery time. Complications may arise from these procedures and often the cosmetic results do not meet the patient's expectations. A hair transplant often may require repetitive procedures that add to the risk of complications and costs.

The present invention includes the following methodologies and preferred compositions for the regrowth of hair by: (1) the injection of autologously cultured dermal papilla fibroblasts and/or dermal papilla-fibroblast-produced extracellular matrix, alone or in conjunction with other epidermal (epithelial) hair follicle cells into or near the dermal papilla area, in or around the hair follicle, into or near the dermal-epidermal junction of skin or injection directly into a "pocket" created in the region to be repaired or augmented of preferably telogen phase hair follicles, although catagen and anagen may confer hair follicle growths, or (2) the surgical engraftment of "hair strands" derived from the aforementioned autologous dermal papilla fibroblasts and/or dermal papilla fibroblast-produced extracellular matrix, alone or in conjunction with other epidermal (epithelial) hair follicle cells which are cultured in such a manner as to form a three-dimensional "tissue-like" structure similar to that which is found in vivo.

Moreover, the present invention also differs on a two-dimensional level in that "true" autologous culture and preparation of the cells is performed by the preferred embodiment that utilizes the patient's own cells and serum for in vitro culture. Preferably telogen phase hair follicles are injected, although catagen phase hair follicles may confer new hair follicle growth and anagen phase hair follicles may maintain the growth of current hair follicle growth. In the preferred embodiment, the area of injection or engraftment is into or near the dermal papilla region of the hair follicle. Other sites may be used, such as along the hair shaft (subcutaneous, reticular dermal, papillar dermal or the shaft rising into the epidermis or the dermal-epidermal junction).

One embodiment of the invention is the injection of expanded hair follicular dermal papilla cells obtained from a skin area of the face where hair grows consistently (beard) and/or the axila and/or the pubic area/and or the thighs into the bald scalp areas (vertex, crown, or bitemporal recessions). This hair follicle dermal papilla cells come from an area or areas of the body induced to growth by the androgenic effect of testosterone.

In a preferred embodiment of the invention, viable expanded autologous dermal papilla cells are obtained from hair follicles located in a skin area of the scalp where hair loss has not occurred or very seldom does. Examples are the areas under the ears or the occipital area. The cultured cells are then injected into the bald scalp areas (vertex, crown, or bitemporal recessions).

SUMMARY OF THE INVENTION

The present invention discloses a methodologies and compositions for the long-term augmentation and/or repair of specific skin defects such as scars, lack of skin tone and skin thinning or need for skin thickening, cellulite, wounds, breast tissue, urological and sphincter structures, preprosthetic soft tissue periodontal disease and disorders, hernia, tendons and ligaments and hair follicles by the injection of two-dimensional or direct surgical placement/implantation of three-dimensional: (1) autologous cultured fibroblasts and/or cultured fibroblast-produced extracellular matix (ECM) preferably derived from connective tissue comprising the area of the tissue defect; (2) autologous cultured fibroblasts and/or cultured fibroblast-produced ECM from other connective tissue sites in the body; (3) cultured fibroblasts and/or cultured fibroblast-produced ECM from juvenile tissue, fetal tissue, non-sun exposed tissue; (4) cultured fibroblasts and/or cultured fibroblast-produced ECM from other individuals or animals. Connective tissue cell types used are fibroblasts derived from (1) dermis or fascia; (2) lamina propria or stromal tissue; (3) dermal papilla from hair follicles; (4) as well as pre-adipocytes from adipose tissue; (5) myofibroblasts from muscle; (6) fibroblasts from ligaments or tendons.

The fibroblast cultures utilized for the augmentation and/or repair of cellulite or scars (e.g. chicken pox) are derived from either dermal, fascial or other connective tissue, in combinations with each other or alone. Other cell types can be pre-adipocytes and/or adipocytes.

Typical scar defects of the skin which can be corrected by the injection or direct surgical placement of the aforementioned autologous cells and/or it's extracellular matrix include areas of scar revision and hypertrophic scarring (e.g. chicken pox). Typical defects of cellulite tissue which can be corrected by the injection or direct surgical placement of the aforementioned autologous cells and/or extracellular matrix include areas of abnormal lumpy/dimple skin appearance mainly in the thighs, hips and buttocks of women. Typical defects of acute or chronic wounds, lost, damaged or diseased tissue, which can be corrected by the injection or direct surgical placement of the aforementioned autologous cells and/or it's extracellular matrix include acute, chronic (pressure, diabetic, venous stasis/ischemic ulcers), partial or full-thickness wounds with intended primary, delayed primary, spontaneous or secondary wound closures. Typical defects of breast tissue which can be corrected by the injection or direct surgical placement of the aforementioned autologous cells and/or it's extracellular matrix include breast reconstruction, contouring and augmentation due to surgically or traumatically injured, congenitally or athestically abnormal, under or overdeveloped breasts. Typical defects of urological tissue which can be corrected by the injection or direct surgical placement of the aforementioned autologous cells and/or it's extracellular matrix include urinary stress incontinence and vesicoureteal reflux by augmenting or repairing the tissue surrounding the urethra and ureters causing a reduction in the abnormally wide and loose lumen. Typical defects of herniated tissue which can be corrected by the injection or direct surgical placement of preferably autologous fascial fibroblasts and/or it's extracellular matrix include accelerated healing by standard surgery, the use as a prosthesis or plug, for use in tandem with current prostheses and in substitution for present transplanted fascial flaps. Typical defects of periodontal tissue which can be corrected by the injection or direct surgical placement of the aforementioned autologous cells and/or it's extracellular matrix include gum and mucosal layer restoration, receded gums, diseased gums (pyorrhea), preprosthetic techniques for healthy periodontal tissue due to stresses of mastication, tooth brushing, trauma form foreign objects, tooth preparation or implants (crowns, bridge, partial or complete dentures), rehabilitation procedures after oral, maxillary or mandibular cancer or tumor resections, physical trauma or reconstructive procedures for congenital cleft palate/lip, mucogingival or alveolar ridge problems, bone protection and preservation and root coverage. Typical defects of ligaments and tendons can be corrected by the injection of ligament or tendon fibroblasts, respectively. Typical defects of hair follicles which can be corrected by the injection or direct surgical placement of the autologous dermal papillary fibroblasts and/or it's extracellular matrix include loss of hair due to primarily androgenetica alopecia.

In a preferred embodiment, cells are injection into the defect. In addition, different cell types can be used in combination with each other.

The use of autologous cultured fibroblasts derived from the various connective tissue sources provides vastly superior post-surgical results. In a preferred embodiment of the present invention, fibroblasts of connective tissue, dermal, or fascial origin as well as pre-adipocytes are derived from full biopsies of the skin. Similarly, lamina propria fibroblasts are obtained from biopsies of the gum or ureteral sphincter area, myofibroblasts are obtained from muscle biopsies and fibroblasts are obtained from tendon or ligament biopsies. It should be noted that the aforementioned biopsy is from the individual who will subsequently undergo the surgical procedure. These tissues are then expanded in vitro utilizing standard tissue culture methodologies.

Additionally, the present invention further provides a methodology of rendering the cultured cells substantially free of non-autologous serum-derived proteins by complete or late-passage of cultured cells in serum-free medium or medium containing the patient's own serum and by repeated washing in phosphate-buffered saline (PBS) or similar physiologically-compatible buffers.

DETAILED DESCRIPTION OF PREFERRED EMBODIMENTS OF THE INVENTION

In one of its embodiments, the invention is A method for repair or augmentation of a tissue defect in a human, said defect selected from the group consisting of a sphincter structure malfunction, presence of cellulite, hypertrophic scars, skin-thinning, skin laxness, a burn, a wound, a hernia, a ligament tear, a tendon tear, baldness, a periodontal disorder, a periodontal disease, and a breast tissue deficiency, which method comprises placing into the tissue at a site within or proximal to the defect site a tissue-defect-correcting-effective or tissue-augmentation-effective quantity of a composition selected from the group consisting of (1) a composition comprising viable mammalian cells from an in vitro culture and (2) a composition comprising cell-produced extracellular matrix from an in vitro culture of mammalian cells.

In another embodiment, the invention is A composition in situ within or proximal to the site of a tissue defect in a tissue of a human and selected from the group consisting of (1) a composition comprising viable mammalian cells from an in vitro culture and (2) a composition comprising cell-produced extracellular matrix from an in vitro culture of mammalian cells, wherein the tissue defect is selected from the group consisting of a sphincter structure malfunction, presence of cellulite, hypertrophic scars, skin-thinning, skin laxness, a burn, a wound, a hernia, a ligament tear, a tendon tear, baldness, a periodontal disorder, a periodontal disease, and a breast tissue deficiency.

The invention will be more fully appreciated from the description herein.

The term "proximal" as to the site at which a composition of the invention is placed to carry out the inventive method will be clearly understood by the skilled to mean near but not exactly at the site of the defect to be repaired or the augmentation to be carried out. Thus, adjacent, subjacent. or above and nearby are included within the term "proximal"

It is to be understood that a composition of the invention is the combination, that occurs for a period of time beginning immediately after a method of the invention is carried out, of the composition which is administered as part of the method and the tissue surrounding the location where this composition is administered.

I. Histology of the Tissues

The skin is composed of two distinct layers: the epidermis a specialized epithelium derived from the ectoderm, and beneath this, the dermis, a vascular dense connective tissue, a derivative of mesoderm. These two layers are firmly adherent to one another and form a region which varies in overall thickness from approximately 0.5 to 4 mm in different areas of the body. Beneath the dermis is a layer of loose connective tissue which varies from areolar to adipose in character. This is the superficial fascia of gross anatomy, and is sometimes referred as the hypodermis, but is not considered to be part of the skin. The dermis is connected to the hypodermis by connective tissue fibers which pass from one layer to the other.

A. Epidermis

The epidermis, a stratified squamous epithelium, is composed of cells of two separate and distinct origins. The majority of the epithelium, of ectodermal origin, undergoes a process of keratinization resulting in the formation of the dead superficial layers of skin. The second component comprises the melanocytes which are involved in the synthesis of pigmentation via melanin. The latter cells do not undergo the process of keratinization. The superficial keratinized cells are continuously lost from the surface and must be replaced by cells that arise from the mitotic activity of cells of the basal layers of the epidermis. Cells which result from this proliferation are displaced to higher levels, and as they move upward they elaborate keratin, which eventually replaces the majority of the cytoplasm. As the process of keratinization continues the cell dies and is finally shed. Therefore, it should be appreciated that the structural organization of the epidermis into layers reflects various stages in the dynamic process of cellular proliferation and differentiation.

I. Dermis

It is frequently difficult to quantitatively differentiate the limits of the dermis as it merges into the underlying subcutaneous layer (hypodermis). The average thickness of the dermis varies from 0.5 to 3 mm and is further subdivided into two strata—the superficial papillary layer and the reticular layer beneath. The papillary layer is composed of thin collagenous, reticular, and elastic fibers arranged in an extensive network. Just beneath the epidermis, reticular fibers of the dermis form a close network into which the basal processes of the cells of the stratum germanium are anchored. This region is referred to as the basal lamina.

The reticular layer is the main fibrous bed of the dermis. Generally, the papillary layer contains more cells and smaller and finer connective tissue fibers than the reticular layer. It consists of coarse, dense, and interlacing collagenous fibers, in which are intermingled a small number of reticular fibers and a large number of elastic fibers. The predominant arrangement of these fibers is parallel to the surface of the skin. The predominant cellular constituent of the dermis are fibroblasts and macrophages. In addition, adipose cells may be present either singly or, more frequently, in clusters. Owing to the direction of the fibers, lines of skin tension, Langer's lines, are formed. The overall direction of these lines is of surgical importance since incisions made parallel with the lines tend to gape less and heal with less scar tissue formation than incisions made at right-angles or obliquely across the lines. Pigmented, branched connective tissue cells, chromatophores, may also be present. These cells do not elaborate pigment but, instead, apparently obtain it from melanocytes.

Smooth muscle fibers may also be found in the dermis. These fibers are arranged in small bundles in connection with hair follicles (arrectores pilorum muscles) and are scattered throughout the dermis in considerable numbers in the skin of the nipple, penis, scrotum, and parts of the perineum. Contraction of the muscle fibers gives the skin of these regions a wrinkled appearance. In the face and neck, fibers of some skeletal muscles terminate in delicate elastic fiber networks of the dermis.

J. Adipose Tissue/Pre-Adipocytes

Fat cells, or adipocytes, are scattered in areolar connective tissue. When adipocytes form large aggregates, and are the principle cell type, the tissue is designated adipose tissue. Adipocytes are fully differentiated cells and are thus incapable of undergoing mitotic division. New adipocytes therefore, which may develop at any time within the connective tissue, arise as a result of differentiation of more primitive cells (pre-adipocytes). Although adipocytes, prior to the storage of lipid, resemble fibroblasts, it is likely that they arise directly from undifferentiated mesenchymal tissue.

Each adipocyte is surrounded by a web of fine reticular fibers; in the spaces between are found fibroblasts, lymphoid cells, eosinophils, and some mast cells. The closely spaced adipocytes form lobules, separated by fibrous septa. In addition, there is a rich network of capillaries in and between the lobules. The richness of the blood supply is indicative of the high rate of metabolic activity of adipose tissue.

It should be appreciated that adipose tissue is not static. There is a dynamic balance between lipid deposit and withdrawal. The lipid contained within adipocytes may be derived from three sources. Adipocytes, under the influence of the hormone insulin, can synthesize fat from carbohydrate. They can also produce fat from various fatty acids which are derived from the initial breakdown of dietary fat. Fatty acids may also be synthesized from glucose in the liver and transported to adipocytes as serum lipoproteins. Fats derived from different sources also differ chemically. Dietary fats may be saturated or unsaturated, depending upon the individual diet. Fat which is synthesized from carbohydrate is generally saturated. Withdrawals of fat result from enzymatic hydrolysis of stored fat to release fatty acids into the blood stream. However, if there is a continuous supply of exogenous glucose, then fat hydrolysis is negligible. The normal homeostatic balance is affected by hormones, principally insulin, and by the autonomic nervous system, which is responsible for the mobilization of fat from adipose tissue.

Adipose tissue may develop almost anywhere areolar tissue is prevalent, but in humans the most common sites of adipose tissue accumulation are the subcutaneous tissues (where it is referred to as the panniculus adiposus), in the mesenteries and omenta, in the bone marrow, and surrounding the kidneys. In addition to its primary function of storage and metabolism of neutral fat, in the subcutaneous tissue, adipose tissue also acts as a shock absorber and insulator to prevent excessive heat loss or gain through the skin. It is a preferred embodiment of this invention that undifferentiated fat cells or pre-adipocytes are used for tissue augmentation/repair.

K. Cellulite

Fat, in the form of triglyceride, is stored in the subcutaneous layer of skin within fat cells (adipocytes). A group of these adipocytes form a fat lobe. Several fat lobes will form a fat lobule that can measure up to 1 cm and is surrounded by blood capillaries. These lobules are located underneath the skin surface and on top of the muscular layer. Connective tissue bands of fibers running perpendicular to the skin connect the surface of the skin to the muscular layer forming pockets that harbor the fat lobes. Excess fat can fill these pockets to a point in which the connective band can not stretch more and hence, will pull the surface of the skin downward. This movement creates dimples, commonly referred to as "cottage cheese", "orange skin" appearance or the "mattress phenomenon". As shown histologically, some degree of inflammation and scarring occurs.

E. Breast Tissue

The breasts are located toward the lateral aspect of the pectoral region, corresponding to the intervals between the third and sixth or seventh ribs and extending from the side of the sternum to the axilla. Their weight and dimensions, as well as the color of the skin covering the areola and nipples, change at different periods of the lifespan and among individuals.

The mammary glands consist of glandular, fat and fibrous or connective tissue, forming hemispherical structures above the Pectoralis Major muscle, separated by a thick sheath of strong connective tissue called the Pectoral Fascia from which suspensory ligaments (Cooper) arise and fan throughout the glandular tissue.

The glandular tissue, responsible for the production of milk during lactation, consists of numerous lobes composed of lobules connected together by areolar tissue, blood vessels and ducts. The smallest lobules formed by alveoli open into lactiferous ducts, from which several form larger ducts and terminate into a single canal or excretory duct (tubuli galactophori), corresponding with one of the chief subdivisions of the gland. There are approximately 15 to 20 excretory ducts converging toward the areola where, before entering into the nipple, form dilatations or ampullae, where milk is stored.

The fibrous or connective tissue invests the entire surface of the breasts and forms septa between the lobes, connecting them together. The fat tissue surrounds the surface of the gland and occupies the spaces between the lobes. The amount of fat varies greatly and determines the form, size and shape of the breasts.

The breasts have a large amount of lymphatics and a large supply of arterial and venous blood from the axillar, intercostal and internal mammary branches.

F. Urological Structures

The male urethra is divided in three regional segments, the prostatic, membranous and penile urethra. One of the membranous urethra (measuring approximately 2.5 cm) muscular layers, the skeletal muscle layer, comprises the external (or voluntary) urinary sphincter, which forms almost a complete ring around the urethral conduit. The membranous urethra is the thickest portion and passes through the genitourinary diaphragm. The altered function of the damaged membranous urethra is to be improved by this invention.

The female urethra is a very short and dilatable tubular structure measuring approximately 4 cm. in length. The urethra begins from the bladder outlet (neck of the bladder) through to the perineal membrane, running behind the pubic symphysis and ending in the external urethral orifice in the perineum. The female urethra represents the entire sphincter mechanism for the bladder. Internally it is covered by a mucous layer and its core is a strong muscular wall composed of mainly three muscular coats. Between the internal and external muscular layers, the middle layer is condensed striated muscle that forms a ring. During incontinence, these fibers are partially deficient in the midline posteriorly, where they fuse into the urethrovaginal septum. Due to its elastic composition and intimate tissue relations to the bladder and mainly the vagina (birth canal during reproductive years), the urethral function may be easily altered or damaged, by anatomical problems of itself and the aforementioned adjacent organs.

The ureter is a muscular conduit that contracts in response to the stretch reflex during transport of the urine from the kidney to the bladder. For the purposes of the invention, the distal ureter and its intravesical and submucosal portions and its orifice into the bladder is the most relevant. This orifice is called the ureteral meatus and is located in the posterolateral aspect of the bladder wall at the sides of the underlying detrusor muscle and the triangular structure called the vesical trigone. The musculature of the ureter and the vesical trigone is in continuity because the ureteral muscular coat passes through the meatus and fans out on the floor of the bladder to form the superficial trigone.

Critical to the normal function of the distal ureter are the lengths of the intravesical ureter and the intrinsic longitudinal muscular coat of the submucosal ureter that inserts into the superficial trigone. These factors are reflected in the appearance of the ureteral orifice normally resembling a cone. When this orifice has a different shape (resembling a horseshoe, golf hole or a stadium) there is an increased tendency for malposition of the orifice (more laterally), abnormal shorter portions of intravesical ureter and hence, reflux as a consequence. Gray H. (1977): Gray's Anatomy, Descriptive and Surgical. A revised American, from the $15^{th}$ English edition. Gramecy Books. New York; Walsh et al, (1998): Campbell's Urology. Seventh Edition. Saunders. Philadelphia; Smith et al. (1996): Smith's Textbook of Endourology. QMP. St. Louis. Mo.

L. Periodontal Anatomy

The human subject is provided by two sets of teeth, which make their appearance at different periods of life. The first set, the temporary, deciduous, or milk teeth, appears in childhood. The second set is permanent, composed of thirty-two teeth: four incisors (two central and two lateral), two canines, four bicuspids, and six molars in each jaw. In general, each tooth consists of three portions: the crown or body, projects above the gum; the root, is entirely concealed within the alveolus; and the neck, the constricted portion, lies between the crown and the root.

The longitudinal section of the tooth from the outside to the center, is comprised of a solid portion consisting of, from the most external cover to the crown: the enamel, a core of dentin and a thin layer of cement covering the root. Inside the core of the dentin layers is a cavity containing the live tissues of the tooth or pulp with blood vessels and nerves.

The neck and root of the tooth are in intimate contact with the surrounding soft tissues. The soft tissue or gum which is a reflection of the mucous membrane from the lips (anterior) and the cheeks (lateral) covers the upper and lower alveolar arches composed by the spaces in the mandibular and maxillar bones, into which the teeth are anchored. The gingiva or gum, is stratified epithelium over a layer of connective tissue known as the lamina propria of the gingiva. Surrounding the roots of the tooth there is an extra layer of connective tissue separating the solid portion of the roots from the soft tissues, called the periodontium or alveolar periosteum.

M. Hernias

The anterior abdominal wall may be considered to have two parts: an anterolateral portion composed of the external oblique, internal oblique, and transverses abdominis muscles; and a midline portion composed by the rectus abdominis and pyramidalis muscles. In the midline, separating the rectus abdominis muscles, exists a tendinous structure called the linea alba, extending from the lower sternum cartilage to the symphysis pubis.

In the anterolateral portion, the flat muscles mentioned above, are arranged so that their fibers are roughly parallel as they approach their insertion on to the rectus sheath. The rectus muscle is enclosed in a stout sheath formed by the bilaminar aponeuroses of the abdominal muscles, which pass anteriorly and posteriorly around the muscle and attach medially to the linea alba.

In the lower quarter of the abdominal wall, the aponeuroses of the internal oblique and transverses abdominis muscles pass anterior to the muscle, which is bounded posteriorly by the transversalis fascia only. The linea semicircularsis of Douglas marks the level at which the rectus sheath loses its posterior wall. This landmark, as well as the umbilical region, represent weak areas of the abdominal wall through which hernias may arise.

The anatomical entities of the groin present a complex arrangement of muscles, fascias and ligaments forming spaces in which hernias are prone to appear. These anatomical findings have many variations among individuals (Schwartz et al., Principles of Surgery, $7^{th}$ Edition, McGraw-Hill. New York, 1999).

The most external structure is the superficial fascia, which is divided into the superficial fascia (Camper's) and a deeper layer divided into three aspects: the Buck's fascia (to the penis), the Dartos (scrotum) and Colles' (perineum). Below the Douglas' line the aponeurosis of the external oblique muscle joins the aponeurosis from the internal oblique and tranversus abdomens to form the anterior layer of the rectus sheath. This fusion of these aponeurotic structures is important because of the contribution to three anatomical entities in the inguinal canal: 1) the Inguinal Ligament (Poupart's) is the thickened lower part of the aponeurosis and runs from the iliac spine to the superior ramus of the pubis; 2) the Lacunar Ligament (Gimbernat's) is the most inferior portion of the inguinal ligament and frequently it forms the medial border of the femoral canal; 3) the reflected inguinal ligament (Colles'), including sometimes the pectineal ligament (Cooper's) is a thick, strong tendinous band fixed to the periosteum of the superior pubic ramus and the periosteum of the ileum laterally.

The inferior portion of the transverses abdominis muscle called the tranversus arch, becomes increasingly less muscular and more aponeurotic as it approaches the rectus sheath. Close to the internal ring (internal opening of the inguinal canal), it is covered by the much more muscular arch of the internal oblique muscle. The tranversalis fascia in the inguinal area is bilaminar, enveloping the epigastric vessels.

The Henle's ligament is a lateral, vertical expansion of the rectus sheath that inserts on the pectin of the pubis. It is present in only 30-50% of individuals and is fused with the tranversus abdominis aponeurosis and transversals fascia (Skandalakis et al.; Surgical Anatomy & Technique, Springer, Verlag, New York, 1995). The Hesselbach's ligament is not a true ligament. It is a thickening of the transversalis fascia at the medial side of the internal ring.

The inguinal canal is an oblique rift measuring approximately four cm in length between its two openings the internal (deep inguinal) ring and the external (superficial inguinal) ring opening. The deep inguinal ring is an opening of the transversalis fascia corresponding to the middle of the inguinal ligament and the superficial ring is on an opening of the aponeurosis of the external oblique lateral and above the pubic crest. The canal contains either the spermatic cord or the round ligament of the uterus. The anterior wall of the canal represents the aponeurosis of the external oblique and laterally the aponeurosis of the internal oblique muscle. The "roof" of the canal is formed by the internal oblique and tranversus abdominis muscles and their aponeuroses. The floor is formed by the inguinal and lacunar (Gimbernat's)

ligaments. The posterior wall is the fusion of the aponeurosis of the transverses abdominis muscles and the transversalis fascia and in 23% of the hernia cases the wall is weak (Mann et al., Bailey & Love's Short Practice of Surgery, $22^{nd}$, Edition., Chapman & Hall Medical, London., 1995, Skandalakis et al.; Surgical Anatomy & Technique, Springer, Verlag, New York, 1995).

I. The Esophagus

The esophagus is a muscular canal, about 8 inches in length extending from the pharynx to the stomach. The esophagus has three coats: an external or muscular coat composed of two groups of thick muscular fibers running longitudinally and circular; a middle or areolar coat of connective tissue which is thick and shows a distinctive layer of smooth muscle forming the muscularis mucosae in contact with the third coat, an internal or mucous coat consisting of a highly dynamic squamus epithelium (Kerr J.: Atlas of Functional histology. Mosby. London, 1999 and Pick T. et al.; Gray's Anatomy. Gramercy Books. New York, 1977 and Dalley A.; Netter's Atlas of Anatomy. Second Edition. Novartis. New Jersey, 1997).

The upper and lower ends of the esophagus have sphincters. The upper sphincter is at the level of the cricoid cartilage. It remains closed by the action of the elastic properties of its walls and by the action of the pharyngeal muscles. In contrast, the lower esophageal sphincter (LES) remains closed because of its intrinsic myogenic tone and a neural pathway of pre- and post-ganglionic neurons. The lower sphincter is not histologically distinct.

Tendons and Ligaments

Tendons and ligaments are dense complex macromolecular networks of connective tissue structures organized in parallel fiber bundles of different types of collagen (~90% of fibrillar collagen type I, less than 10% being collagen type III and traces of other types of collagen) containing large amounts of water (making for ⅔ of their weight). Tendons anchor the muscles to bones or into the joints (Kerr J: Atlas of Functional Histology. Mosby. London, 1999 and Duthie R. et al., Mercer's Orthopedic Surgery. Ninth Edition. Arnold. London, 1996). Ligaments keep together the different bony or cartilaginous structures of a joint providing stability and mobility to it. Muscles, tendons, ligaments and bones comprise units, and an injury to one component of the unit affects it as a whole.

I. Hair Follicle

The hair follicle changes shape and structure during the different phases of the growth cycle. The hair follicle undergoes through three main phases: 1) anagen, the active growing phase, 2) catagen, a transitional phase and 3) telogen, a quiescent phase (Percoraro et al., J Invest Dermatol, 43:145, 1964, Adachi et al., Curr Probl Dermatol, 5:37, 1973, Peus et al, Dermatol Clin, 14:559, 1996).

In the anagen phase, the follicle has a long tubelike structure and is divided into the upper and lower sheath. The upper sheath retains its structure during all the phases, while the lower sheath undergoes the cyclic remodeling changes of the hair follicle. Hence, follicular accessory structures (sebaceous gland, erector muscle, sensory nerve and the apocrine gland's duct) remain intact. The lower sheath, including the bulb of the hair follicle, is a characteristic structure of the anagen follicle. It holds the bulbar matrix cells (follicular germ cells seeded during embryological folliculogenesis), which proliferate and migrate upward differentiating into three major groups: hair matrix, inner and outer sheath. The hair matrix further differentiates into the medulla, hair cortex and cuticle. The inner sheath forms the cells that constitute the inner wall of the pillory canal. The outer sheath cells differentiate into cuboidal cells that store large amounts of glycogen as energy source. In the follicular bulb, melanocytes can be observed and although they do not migrate, their products (pigments) do travel into hair cortical cells. The dermal papilla is the core of the bulb and is composed of mainly fibrocystic cells and blood vessels. During anagen this structure provides for blood circulation and bulbar cell differentiation and penetrate the dermal layer into the subcutaneous layers. The average duration of the anagen phase is 3 years.

Early and mid-anagen is characterized by great activity in the lower sheath of the follicle where the germ cells that remained dormant after catagen and during telogen phases begin to grow. Mitotic cell proliferation and addition of mesenchymal cells are observed until a new bulbar structure is observed and starts to produce a new hair matrix and an inner and outer root sheath that connects the anchoring telogen follicle. The mid-anagen phase ends with a new, fully developed hair in which the old club hair emerging from the same area through the same pillory canal is shed. Thus, a replacement of old hair with new hair by cyclic turnover usually occurs without loss of hair.

Catagen is the involution phase involving the autophagy (self-absorption) of the follicular epithelial cells, destroying almost all the lower sheath of the follicle in approximately one week, while the dermal papillary cells transit into a mesenchymal-type cell. The bulbar cells are replaced by proliferating perifollicular connective tissue cells and a thick proteinaceous hyaline membrane (vitreous membrane). The induction mechanism of the catagen phase is not known. However, drugs that inhibit mitosis, such as cyclophosphamide and colchicine, or radiation, can induce the premature catagen phase. The duration of catagen can be several months.

During the resting phase, telogen, the hair bulb produced from anagen remains in the upper follicular sheath, while the lower tip of the keratinized hair cortex is tightly attached to the epidermal cells of the upper follicular sheath. This club hair does not shed until a new hair emerges from a new anagen follicle. The telogen follicles consist of simple epidermal sheaths and they hold the hair and also anchor the base of a new anagen follicle. The duration of telogen phase varies greatly with the region of the body, sex, age, and ethnicity. In the scalp it is known that the average duration of telogen is about 100 days.

III. Methodologies

A. In vitro Cell Culture of Dermal, Fascial, Stromal or Lamina Propria, Myofibroblasts, Dermal Papilla Fibroblasts, Pre-Adipocytes or Chondrocytes While the present invention may be practiced by utilizing any type of non-differentiated mesenchymal cell found in a connective tissue source which can be expanded by in vitro culture, fibroblasts derived from dermal, fascial lamina proprial tissue, dermal papilla fibroblasts from the bulbar area of the hair follicle, fibroblasts from other connective tissue, or pre-adipocytes from subcutaneous or adipose tissue are utilized in a preferred embodiment due to their relative ease of isolation and in vitro expansion in tissue culture. In general, tissue culture techniques which are suitable for the propagation of non-differentiated mesenchymal cells may be used to expand the aforementioned cells/tissue and practice present invention as further discussed below. See e.g., Culture of Animal Cells: A Manual of Basic Techniques, Freshney, R. I., ed., (Alan R. Liss & Co., New York 1987); Animal Cell Culture: A Practical Approach, Freshney, R. I. ed., (IRL Press, Oxford, England (1986), whose references are incorporated herein by reference.

The utilization of autologous placement of cells or culture cell-produced extracellular matrix is a preferred composition of the invention. Autologous cells (i.e., those derived directly from the patient) are initially obtained from a tissue sample via biopsy directly from the patient who will be undergoing the corrective surgical procedure. Subsequently fibroblasts derived from the dermal, fascial, or lamina propria regions, bulbar area of hair follicles, cartilage, muscle or adipose tissue are cultured.

While the following sections will primarily discuss the autologous culture of fibroblasts of dermal fascial or connective tissue origins, in vitro culture of other fibroblasts from lamina propria or muscle tissue, bulbar area of hair follicles and pre-adipocytes from adipose tissue may fibroblast culture is preferably initiated by the following methodology. A full-thickness biopsy of the skin (~3×6 mm) is initially obtained through, for example, a punch biopsy procedure. The specimen is repeatedly washed with antibiotic and anti-fungal agents prior to culture. Through a process of sterile microscopic dissection, the keratinized tissue-containing epidermis and subcutaneous adipocyte-containing tissue is removed, thus ensuring that the resultant culture is substantially free of non-fibroblast cells (e.g., adipocytes and keratinocytes). The isolated adipocytes-containing tissue may then be utilized to establish pre-adipocyte cultures. Micro-dissection can be performed on hair follicles to isolate the bulbar region containing the dermal papilla fibroblasts. Alternately, whole tissue may be cultured and fibroblast-specific growth medium may be utilized to "select" for these cells.

Two methodologies are generally utilized for the autologous culture of fibroblasts in the practice of the present invention—mechanical and enzymatic. In the mechanical methodology, the fascia, dermis, lamina propria, other connective tissue or adipose tissue is initially dissected out and finely divided with scalpel or scissors. The finely minced pieces of the tissue are initially placed in 1-2 ml of medium in either a 5 mm petri dish (Costar), a 24 multi-well culture plate (Corning), or other appropriate tissue culture vessel.

Incubation is preferably performed at 37 deg. C. in a 5% $CO_2$ atmosphere and the cells are incubated until a confluent monolayer of fibroblasts has been obtained. This may require up to 3 weeks of incubation. Following the establishment of confluence, the monolayer is trypsinized to release the adherent fibroblasts from the walls of the culture vessel. The suspended cells are collected by centrifugation, washed in phosphate-buffered saline, and resuspended in culture medium and placed medium.

In a preferred embodiment of the enzymatic culture methodology, pieces of the finely minced tissue are digested with a protease for varying periods of time. The enzymatic concentration and incubation time are variable depending upon the individual tissue source. The initial isolation of the fibroblasts from the tissue, as well as the degree of subsequent outgrowth of the cultured cells, are highly dependent upon these two factors. Effective proteases include, but are not limited to, trypsin, chymotrypsin, papain, chymopapain, and similar proteolytic enzymes. Preferably, the tissue is incubated with 200-1000 U/ml of collagenase type II for a time period ranging from 30 minutes to 24 hours, as collagenase type II was found to be highly efficacious in providing a high yield of viable fibroblasts. Following enzymatic digestion, the cells are collected by centrifugation and resuspended into fresh medium in culture flasks.

Various media may be used for the initial establishment of an in vitro culture of human fibroblasts. Dulbecco's Modified Eagle Medium (DMEM, Gibco/BRL Laboratories) with concentrations of fetal bovine serum (FBS), cosmic calf serum (CCS), and in a preferred embodiment, the patient's own serum varying from 0.5-20% (v/v)—with higher concentrations resulting in faster culture growth—, or serum free media, are readily utilized for fibroblast culture. In addition, the complete culture medium typically contains L-glutamine, sodium bicarbonate, pyridoxine hydrochloride, 1 g/liter glucose, and gentamycin sulfate. The use of the patient's own serum mitigates the possibility of pathogens and subsequent immunogenic reaction due to the presence of constituent antigenic proteins in the other serums.

Establishment of a fibroblast cell line from an initial human biopsy specimen generally requires 2 to 3.5 weeks in total. Once the initial culture has reached confluence, the cells may be passaged into new culture flasks following trypsinization, or mechanical/chemical dissociation done by standard methodologies known within the relevant field. Preferably, for expansion, cultures are "split" 1:3 or 1:4 into T-150 culture flasks (Corning) yielding ~$5\times10^7$ cells/culture vessel. The capacity of the T-150 culture flask is typically reached following 5-8 days of culture at which time the cultured cells are found to be confluent or near confluent.

Cells are preferably removed for freezing and long-term storage during the early passage stages of culture, rather than the later stages due to the fact that human fibroblasts are capable of undergoing a finite numbers of passages. Culture medium containing 80% DMEM growth medium, 10% (v/v) serum, and 10% (v/v) tissue culture grade dimethylsulfoxide (DMSO, Gibco/BRL) may be effectively utilized for freezing of fibroblast cultures. Frozen cells can subsequently be used to inoculate secondary cultures to obtain additional fibroblasts for use in the original patient, thus doing away with the requirement to obtain a second biopsy specimen.

To minimize the possibility of subsequent immunogenic reactions in the engraftment patient, the removal of the various antigenic constituent proteins contained within the serum may be facilitated by collection of the fibroblasts by centrifugation, washing the cells repeatedly in phosphate-buffered saline (PBS) and then either re-suspending or culturing the washed fibroblasts for a period of 2-24 hours in serum-free medium containing requisite growth factors which are well known in the field. Culture media include, but are not limited to, Fibroblast Basal Medium (FBM). Preferably and alternatively, the fibroblasts may be cultured utilizing the patient's own serum in the appropriate growth medium.

After the culture has reached a state of confluence or sub-confluence, the fibroblasts may either be processed for injection or further cultured to facilitate the formation of a three-dimensional "tissue" for subsequent surgical engraftment. Fibroblasts utilized for injection consist of cells suspended in a collagen gel matrix or extracellular matrix, preferably from obtained from the autologous cells grown in vitro. The collagen gel matrix is preferably comprised of a mixture of 2 ml of a collagen solution containing 0.5 to 1.5 mg/ml collagen in 0.05% acetic acid, 1 ml of DMEM medium, 270 μl of 7.5% sodium bicarbonate, 48 microliters of 100 micrograms/ml solution of gentamycin sulfate, and up to $5\times10^6$ fibroblast cell/ml of collagen gel. Following the suspension of the fibroblasts in the collagen gel matrix, the suspension is allowed to solidify for approximately 15 minutes at room temperature or 37 deg C. in a 5% $CO_2$ atmosphere. The collagen may be derived from human or bovine sources, or preferably from the patient and may be enzymatically- or chemically-modified (e.g., atelocollagen).

Three-dimensional "tissue" is formed by initially suspending the fibroblasts in the collagen gel matrix as described above. Preferably, in the culture of three-dimensional tissue, full-length collagen (preferably obtained from the autologous cells grown in vitro) is utilized, rather than truncated or modified collagen derivatives. The resulting suspension is then placed into a proprietary "transwell" culture system which is typically comprised of a culture well in which the lower growth medium is separated from the upper region of the culture well by a microporous membrane. The microporous membrane typically possesses a pore size ranging from 0.4 to 8 μm in diameter and is constructed from materials including, but not limited to, polyester, nylon, nitrocellulose, cellulose acetate, polyacrylamide, cross-linked dextrose, agarose, or other similar materials. The culture well component of the transwell culture system may be fabricated in any desired shape or size (e.g., square, round, ellipsoidal, etc.) to facilitate subsequent surgical tissue engraftment and typically holds a volume of culture medium ranging from 200 μl to 5 ml. In general, a concentration ranging from $0.5 \times 10^6$ to $10 \times 10^6$ cells/ml, and preferably $5 \times 10^6$ cells/ml, are inoculated into the collagen/fibroblast-containing suspension as described above. Utilizing a preferred concentration of cells (i.e., $5 \times 10^6$ cells/ml), a total of approximately 4-5 weeks is required for the formation of a three-dimensional tissue matrix. However, this time may vary with increasing or decreasing concentrations of inoculated cells. Accordingly, the higher the concentration of cells utilized, the less time for tissue formation, due to a higher overall rate of cell proliferation and replacement of the exogenous collagen with endogenous collagen and other constituent materials which form the extracellular matrix synthesized by the cultured fibroblasts. Constituent materials which form the extracellular matrix include, but are not limited to, collagen, elastin, fibrin, fibrinogen, proteases, fibronectin, laminin, fibrellins, ground substance and other similar proteins. It should be noted that the potential for immunogenic reaction in the engrafted patient is markedly reduced due to the fact that exogenous collagen used in establishing the initial collagen/fibroblast-containing suspension is gradually replaced during subsequent culture by endogenous collagen and extracellular matrix materials synthesized by the fibroblasts.

B. In Vitro Culture of Adipocytes or Chrondocytes

Pre-adipocytes require a "feeder-layer" or other type of solid support on which to divide and grow. Plastic substrates, solid supports made of collagen gel or culture extracellular matrix can be used to grow pre-adipocytes. In general, the in vitro culture of pre-adipocytes is performed by the mechanical or enzymatic disaggregation of the adipocytes from adipose tissue derived from a biopsy specimen. The pre-adipocytes are "seeded" onto the surface of the aforementioned solid support or plastic substrates and allowed to grow until near-confluence is reached. Near-confluence to confluence induce the conversion into adipocytes. The adipocytes are removed by gentle scraping or gentle enzymatic treatment of the solid surface.

Chondrocytes are obtained from cartilage slices from the patient. The extraction site can be any cartilage bearing area of the body such as the ears or joints. Cartilage isolated from a small 3×6 mm ear punch biopsy or through arthroscopic surgery of a knee is chilled in sterile saline solution, washed three times Ham's F12 medium containing 10 mM HEPES buffer, 70 uM gentamicin sulfate, 2.2 uM amphotericin B and 300 uM L-ascorbic acid. The cartilage is minced and then incubated for 16 hours in clostridial collagenase (150 U/L) and deoxyribonuclease 1 (25,000 μL). Cells were then filtered through a nylon mesh (25 uM pore diameter) and resuspended in serum supplemented media for cell culture growth, see Brittberg, M., et al., The New England Journal of Medicine, 331, No. 14, 879-895, 1994.

C. Isolation of the Extracellular Matrix

The extracellular matrix (ECM) may be isolated in either a cellular or acellular form. Constituent materials which form the ECM include, but are not limited to, collagen, elastin, fibrin, fibrinogen, proteases, fibronectin, laminin, fibrellins, ground substance and other similar proteins. ECM is typically isolated by the initial culture of cells derived from a biopsy of skin (reticular and/or papillary dermis), subcutaneous tissue (adipose tissue and fascia), lamina propria or bulbar hair follicle tissue, as previously described. After the cultured cells have reached a minimum of 25-50% sub-confluence, the ECM may be obtained by mechanical, enzymatic, chemical, or denaturant treatment. Mechanical collection is performed by scraping the ECM off of the plastic culture vessel and re-suspending in phosphate-buffered saline (PBS). If desired, the constituent cells are lysed or ruptured by incubation in hypotonic saline containing 5 mM EDTA. Preferably, however, scraping followed by PBS re-suspension is generally utilized. Enzymatic treatment involves brief incubation with a proteolytic enzyme such as trypsin. Additionally, the use of detergents such as sodium dodesyl sulfate (SDS) or treatment with denaturants such as urea or dithiothreitol (DTT) followed by dialysis against PBS, will also facilitate the release of the ECM from surrounding associated tissue.

The isolated ECM may then be utilized as a "filler" material in the various augmentation or repair procedures disclosed in the present application. The ECM can serve as a support for autologous cells or as a means to contain the cells in the tissue defect being repaired/augmented, in the form of a physically pressed matrix mesh that is either fresh or frozen dried. In addition, the ECM may possess certain cell growth- or metabolism-promoting characteristics.

D. In vitro Culture of Fetal or Juvenile Cells or Tissues

In another preferred embodiment, rather than utilizing the patient's own tissue, all of the aforementioned cells, cell suspensions, or tissues may be derived from fetal or juvenile sources or sources that have been exposed to the sun little, or not at all, and in any case, less than the tissue being repaired. An acellular ECM may also be obtained from fetal ECM by hypotonic lysing of the constituent cells. The acellular ECM derived from fetal or juvenile or less sun-exposed sources or from in vitro culture of early passage cells typically differs in both quantity and characteristics from that of the ECM derived from senescent or late-passage cells. The cellular or acellular ECM derived from fetal or juvenile sources may be used as a "filler" material in the various augmentation or repair procedures disclosed in the present application. In addition, the fetal or juvenile ECM may possess certain cell growth- or metabolism-promoting characteristics. In addition, the fetal or juvenile ECM may be used in conjunction with the fetal or juvenile source's cells.

E. Injection of Cultured Fibroblasts, Pre-Adipocytes, Chondrocytes or Extracellular Matrix and Placement of Three-Dimensional Matrix ("Strands")

The procedures listed below may be performed under general, local, topical, monitored, or with no anesthesia, depending upon patient compliance and tolerance, the amount of injected or placed material, and the type of injection or engraftment performed.

To augment or repair dermal defects, cultured fibroblasts are injected initially into the lower dermis, next in the upper and middle dermis, and finally in the subcutaneous regions of the skin as to form raised areas or "wheels." The fibroblast suspension is injected via a syringe with a needle ranging from 30 to 18 gauge, with the gauge of the needle being dependent upon such factors as the overall viscosity of the fibroblast suspension and the type of anesthetic utilized. Preferably, needles ranging from 22 to 18 gauge and 30 to 27 gauge are used with general and local anesthesia, respectively.

To inject the fibroblast suspension into the lower dermis, the needle is placed at approximately a 45° angle to the skin with the bevel of the needle directed downward. To place the fibroblast suspension into the middle dermis the needle is placed at approximately a 20-30° angle. To place the suspension into the upper dermis, the needle is placed almost horizontally (i.e., 10-15° angle). The dermal injections can be staggered subjacent to the defect area or accomplished by initial placement of the needle into the dermal tissue and injection of the fibroblast suspension during subsequent needle withdrawal. Injections into the subcutaneous layer, fascia and muscle can be accomplished in a similar fashion. In addition, it should be noted that the needle is preferably inserted into the skin from various directions such that the needle tract will be somewhat different with each subsequent injection. This technique facilitates a greater amount of total skin area receiving the injected fibroblast suspension.

Following the aforementioned injections, the skin should be expanded and possess a relatively taut feel. Care should be taken so as not to produce an overly hard feel to the injected region. Preferably, the defect area appears elevated following injection and should be "overcorrected" by a slight degree of over-injection of the fibroblast suspension, as typically some degree of settling or shrinkage will occur post-operatively.

In some scenarios, the injections may pass into deeper tissue layers, including the fascia and muscle To augment or repair depressed or hypertrophic scars (e.g., chicken pox) or cellulite, among other skin defects, the preferred injection will be that which replicates the in vivo situation first. Thus, injections (e.g. 45° angle) of fascial fibroblasts deep into the subcutaneous layer of skin and into the muscle subjacent to the defect, similarly angled injection of pre-adipocytes/adipocytes into the subcutaneous layer of skin and injection of reticular dermal fibroblasts into the middle and lower layers and papillary fibroblasts into the upper dermal layer at the prescribed angles are the preferred method of treatment. Other combinations of cells/ECM, single types of cells/ECM and injection(s) into separate or single layers, that are functional and more convenient, but less similar than that which occurs in vivo, can also be applied effectively.

Additionally, for the treatment of cellulite, the connective tissue strands that transverse the adipose tissue may be severed, displaced or rearranged in conjunction with injections of cells and/or ECM.

To augment or repair the various types of wounds and to improve the healing process in acute, primary closure full-thickness surgical wounds, in particular patients with high risk of wound complications (obese, poor developed muscular or fascia tissues in abdominal wounds, long and traumatic surgical procedures, etc) injection into the dermis and deeper layers (subcutaneous, fascia) adjacent, subjacent or within the wound's margins or "pockets" created in the wound's margins with cells and/or extracellular matrix and/or blood serum or clot, is preferred. The injection may be followed by a suitable closure technique (sutures, staples, tape etc.) or the injected material into the area may be sealed by suturing of the area tissue, alone or in conjunction with an ECM mesh, gauze or other physiological acceptable substance.

Injections adjacent to, subjacent to, or into the dermis and deeper layers (subcutaneous, fascia) of the wound's bed or margins or "pockets" created in the wound's margins or bed with cells and/or extracellular matrix and/or blood serum and/or clot is a method for the improvement and acceleration of healing conditions in uninfected delayed primary closure wounds, chronic wounds such as pressure, diabetic, venous stasis, ischemic ulcers and full-thickness burns and may require repetitive injections or applications into the wound margins and/or wound bed or "pocket". Wound dressings containing hydrocolloids and hydrogels to promote humidity and/or debriding agents to increase granulation and/or healing enhancing compounds such as foams, absorptive powders or pastes of calcium alginate or biologicals such as collagen and/or tissue growth factors and/or biodegradable microspheres and/or natural clotting agents can be used in conjunction with the autologous cells and/or ECM. The dressing can be made of skin "like" layer (mesh) of freeze-dried or fresh pressed cellular or acellular ECM, to cover and protect the wound bed and promote granulation.

In a preferred methodology utilized to augment or repair the scars and/or cellulite and/or wounds by the surgical placement of autologously cultured dermal and/or fascial fibroblast three-dimensional tissue or "strands", a needle (the "passer needle") is selected which is larger in diameter and greater in length than the area to be repaired or augmented. The passer needle is then placed into the skin and threaded down the length of the area. Guide sutures are placed at both ends through the dermal or fascial fibroblast strand. One end of the guide suture is fixed to a needle which is subsequently placed through the passer needle. The guide suture is brought out through the skin on the side furthest (distal point) from the initial entry point of the passer needle. The dermal or fascial fibroblast graft is then pulled into the passer needle and its position may be adjusted by pulling on the distal point guide suture or, alternately, the guide suture closest to the passer needle entry point. While the dermal or fascial strand is held in place by the distal point suture, the passer needle is pulled backward and removed, thus resulting in the final placement of the graft following the final cutting of the remaining suture. Fascial or dermal grafts can be placed in either the subcutaneous, dermal or fascial layers for many of the skin defects to be augmented or repaired. Similar grafts can be placed in the dermal and subcutaneous layers for treating cellulite. Fascial and dermal grafts can be placed in the dermal, subcutaneous, fascial and subjacent areas of the wound area.

If the area for augmentation or repair is either smaller or larger than would be practical to fill with the aforementioned needle method, or if a greater degree of augmentation is needed, a "pocket" may be created with a scalpel, scissors, or other similar instrument. A strand of three-dimensional tissue (e.g. dermis or fascia) is then threaded into this area by use of guide sutures and passer needle, as described above or cells and/or ECM is injected or placed in the pocket and closed by adhesives, sutures, laser or similar methods.

To contour, firm, repair or augment breast tissue, shape and size, cells and/or ECM are injected under local anesthesia, into the various layers of skin in the four breast quadrants, the reticular and/or papillary dermis, the subcutaneous layers including adipose tissue and the fascial layer, muscle or into "pockets" created for cell and/or ECM placement. Injection into the underlying breast layers into the fascia covering the muscle is accomplished by use of injection needles of the smallest possible gauge which will accommodate the injectate without the use of extraneous pressure during the actual injection process. This is a subjective process as to the overall "feel" and the use of too much pressure may irreparably damage the injected cells. The material is injected via a syringe with a needle ranging from 30 to 27 gauge, with the gauge of the needle being dependent upon such factors as the overall viscosity of the injectate and the type of anesthetic utilized. Preferably, fine needles ranging from 30 to 24 gauge may be are used to prevent traumatic injury of vessels and hematomas during the procedure. Several injections may be performed. Application of the invention can be carried out under general anesthesia by embedding an ECM pressed freeze-dried mesh or fresh pressed mesh with or without cells and introduce it into breast "pockets" of the subcutaneous, fat or fascial layers, made by surgical small incisions and then pushed up into the superior quadrants of the breasts.

For injection into ureteral structures the preferred route to practice the invention is through performing routine outpatient or even office cystoscopy, during which the cystoscope is introduced into the urethra and its tip is located at a proper visual distance from the abnormal distended urethra/ureter lumen and a 20 gauge needle is used by either of the following two methods for urinary incontinence: 1) Introducing the needle through the working channel of the cystoscope and orienting it into the urethral surrounding tissue from the distended lumen to the outside, advancing it and then injecting the preparation until the ideal narrowing of the lumen is achieved. This is the preferred method of injection for the incontinent male. 2) Periurethrally, directing the needle with the bevel downward, advancing it to the bladder neck with the direction of the needle placement guided by the axis of the cystoscope. Observation of the ideal needle placement into the surrounding mucosal tissue can be obtained by gentle movements of the needle to be observed from the cystoscopic visual field before injecting the cell preparation packed into a syringe connected into the needle. The ideal narrowing lumen effect of the injected preparation should be continually monitored by the cystoscope until the injection is complete. Injection is delivered at the three or nine o'clock positions. Regardless of the technique used, the autologous cell and/or ECM preparation is placed within the wall of the urethra (intraurethral). This is the preferred method to best practice the invention for women with urinary incontinence.

Patients with vesicoureteral reflux are treated after the patient is positioned in dorsal lithotomy and the cystoscope is advanced and the ureters are visualized. A 20-gauge needle is advanced through the working channel. The needle tip is inserted under direct vision at a six o'clock position into the subureteral space, approximately 4 to 6 mm distal to the ureteral orifice. Occasionally proper placement of the needle may be facilitated by placing a 3 Fr catheter into the ureter. The needle is then advanced proximally. The autologous cell and/or ECM preparation is then injected slowly until a bulge nearly obliterates the ureteral orifice. Care must be exercised in performing a single precise injection because if multiple ones are needed the material will be lost due to extravasation. The needle is kept in position for 2-3 minutes before withdrawal for the same reason.

A video urodynamic study was performed on a patient. The patient had been diagnosed as suffering from bilateral vesicoureteral reflux, grade III bilaterally.

1.5 ml of 20 million autologous dermal fibroblasts from the patient's skin biopsy was split and injected by cystourethroscopy at the 6-7 position under each ureteral orifice. Excellent coaptation with no bleeding was noted. The procedure was performed without complication.

Urodynamic tests at seven weeks after the procedure indicated the injection resulted in significant improvement without complication. In particular, cystostomy was performed and under gravity fill up to 300 ml there was no change in appearance of the bladder and no reflux under pumpkin fusion per urodynamic machine at a rate of 50 ml per minute. At 450 ml, there was Grade I left vesicle ureteral reflux, but no reflux on the right side at all.

Further urodynamic tests six months after the procedure indicated there was no reflux on the right or left side at all.

An alternative use of the invention during open surgery to treat stress urinary incontinence and vesicoureteral reflux in men and women is the injection of the autologous cells and/or ECM to reinforce the surgically repaired tissues and prevent the frequently reversible poor results of the surgical treatments (e.g. bladder neck, urethral region, surgical sutures elevating periurethral tissue to be fixed to the pubic bone for female incontinence).

To repair herniated abdominal wall tissue, the placement of "strands" derived from autologous dermal and/or fascial fibroblasts are shaped into a mesh like form and are placed on the defect through a small surgical incision under local anesthesia. An alternative use of the invention is the combination of a routine "tension free" technique with the insertion of a prosthetic mesh in conjunction with the injection of the cultured cells, preferably fascial fibroblasts around the mesh. The invention can be combined with traditional surgical methods to stitch together the sides of the defect with the injection of the autologous cultured cells and/or extracellular matrix. Fascial flaps made of the autologous fascial cells and/or extracellular matrix can replace mesh implants, be used for layer closure techniques or be sutured into the fascial layers of the hernia tissues and to muscle for closure of the hernia. To repair, contour or augment periodontal tissue, several treatment techniques are available to the connective tissue. In the presence of a small defect, such as an alveolar ridge augmentation, the autologous cells and/or ECM can be injected under local anesthesia by means of the use of a fine needle gauge 22 to 24, positioned perpendicular (90° angle) to the neck of the tooth if present, and advancing the needle by positioning it sub-epithelial, into the lamina propia region of the gingiva and injecting the autologous cells and/or ECM. For free gingival partial or complete thickness graft or sub-epithelial graft, the invention is best carried on by engraftment and suture of a cellular or acellular mesh, pressed fresh or freeze-dried ECM.

Injections or placements of autologous cells and/or ECM are also used when the presence of mucogingival or alveolar ridge problems are present as well as when bone protection and preservation, tooth implant integration or root coverage by means of gum augmentation (lamina propria of the gingiva or the periodontium) have to be achieved.

For the production of hair growth, autologous dermal papilla cells and/or extracellular matrix derived from these cells are injected or implanted into the bulbar region (dermal papilla) or along the outer sheath of the vellus hairs or regions surrounding the vellus hairs or in the dermal layer of the scalp, preferably in the papillary layer towards epidermal junction. Injections, after anesthesia, can be performed with a syringe with small gauge needle, 30 gauge or smaller, or with microdissection needles, under magnification with a lens or a stereoscope. The fibroblasts can be delivered by injection into the hair follicle or pore in which the follicle resides. Additionally, the fibroblasts can be delivered by the massaging of a biological solution or salve containing the fibroblasts into the scalp area. A "pocket" or wound space can be created by means of a small incision with a surgical scalpel or other fine cutting instrument into the scalp area. The dermal papilla cells are positioned into the space, preferably in contact with hair epidermal cells, such as the cells in the outer root sheath, although the placement of cells towards the epidermal junction or into deeper layers can also be conducted. A suture (polymer, biodegradable) closing the incision or covering the ECM mesh containing the cells may close the "pocket".

A hypertrophic scar, namely a chicken pox scar, was repaired according to the invention in a patient. The scar was on the right side close to the nose bridge. ~2.5 million dermal fibroblasts which were grown autologously from fibroblasts of the patient were trypsinized and suspended for injection. The cells were injected into the upper, mid, lower dermis at the site of the scar. The procedure and follow-up entailed no complications. Three weeks after the procedure the scar was gone.

While embodiments and applications of the present invention have been described in some detail by way of illustration and example for purposes of clarity and understanding, it would be apparent to those individuals whom are skilled within the relevant art that many additional modifications would be possible without departing from the inventive concepts contained herein.

The invention claimed is:

1. A method for removing a hypertrophic scar in a human patient comprising introducing a suspension of human fibroblasts at or proximal to a hypertrophic scar in said patient after said fibroblasts have been expanded in vitro in a suitable culture media, wherein said suspension contains sufficient number of said fibroblasts to remove said hypertrophic scar.

2. The method of claim 1 wherein said fibroblast are obtained from a skin biopsy.

3. The method of claim 1 wherein said fibroblasts are autologous.

4. The method of claim 1 wherein said culture media contains autologous serum.

* * * * *